(12) United States Patent
Schumaier

(10) Patent No.: US 12,069,435 B2
(45) Date of Patent: Aug. 20, 2024

(54) HEARING PROTECTION, NOISE MEASUREMENT AND COMMUNICATION SYSTEM

(71) Applicant: Daniel R. Schumaier, Elizabethton, TN (US)

(72) Inventor: Daniel R. Schumaier, Elizabethton, TN (US)

( * ) Notice: Subject to any disclaimer, the term of this patent is extended or adjusted under 35 U.S.C. 154(b) by 0 days.

(21) Appl. No.: 18/420,313

(22) Filed: Jan. 23, 2024

(65) Prior Publication Data

US 2024/0163619 A1 May 16, 2024

Related U.S. Application Data

(60) Continuation-in-part of application No. 18/524,562, filed on Nov. 30, 2023, now Pat. No. 11,962,977, which is a continuation-in-part of application No. 17/966,775, filed on Oct. 15, 2022, now Pat. No. 11,856,368, which is a division of application No. 17/887,548, filed on Aug. 15, 2022, now Pat. No. 11,546,702.

(51) Int. Cl.
H04R 25/00 (2006.01)

(52) U.S. Cl.
CPC ..... *H04R 25/505* (2013.01); *H04R 2225/025* (2013.01); *H04R 2225/61* (2013.01)

(58) Field of Classification Search
None
See application file for complete search history.

(56) References Cited

U.S. PATENT DOCUMENTS

| | | | |
|---|---|---|---|
| 4,985,925 A | 1/1991 | Langberg et al. |
| 6,661,901 B1 | 12/2003 | Svean et al. |
| 7,024,010 B2 | 4/2006 | Saunders et al. |
| 7,512,243 B2 | 3/2009 | Haussmann |
| 10,045,133 B2 | 8/2018 | Bauman et al. |
| 10,937,407 B2 | 3/2021 | Goldstein |
| 2012/0087511 A1 | 4/2012 | Lumsden et al. |
| 2016/0255449 A1 | 9/2016 | Bauman et al. |
| 2020/0288251 A1 | 9/2020 | Kuipers |
| 2021/0052429 A1 | 2/2021 | Dittrich et al. |

*Primary Examiner* — Kenny H Truong
(74) *Attorney, Agent, or Firm* — Luedeka Neely, P.C.

(57) ABSTRACT

A hearing protection system includes an earplug and an electronic hearing device inserted into a cavity in the earplug. The electronic hearing device includes electronics that incorporate digital signal processing to provide sound amplification and fast compression programming to shut off sound amplification to protect the user when a loud noise is detected. The housing of the electronic hearing device has a sound aperture for emitting the sound from a speaker assembly. The sound aperture is aligned with an opening of a sound tube in the earplug so that sound generated by the speaker assembly can propagate through the sound tube to the user's ear canal. The electronic hearing device may include a short-range communication interface for receiving a short-range communication signal that carries information. The system may include a noise dosimeter that generates noise exposure measurement data related to a dose of noise exposure over a period of time.

13 Claims, 23 Drawing Sheets

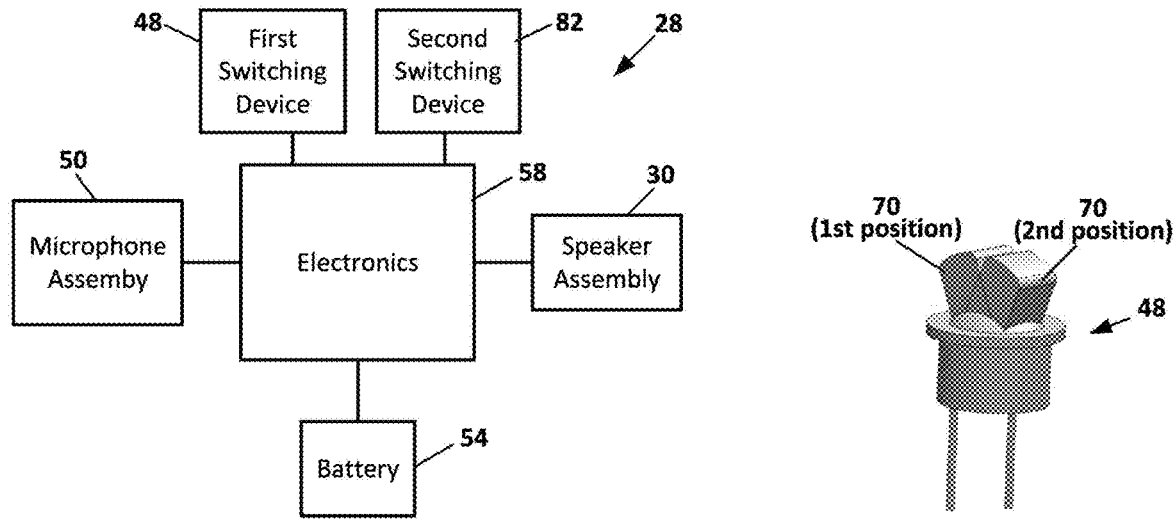
FIG. 9
FIG. 10
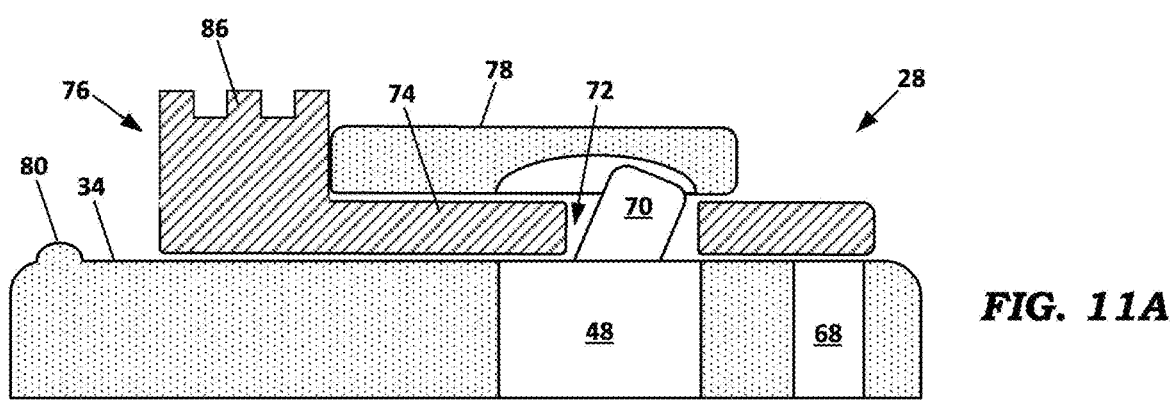
FIG. 11A
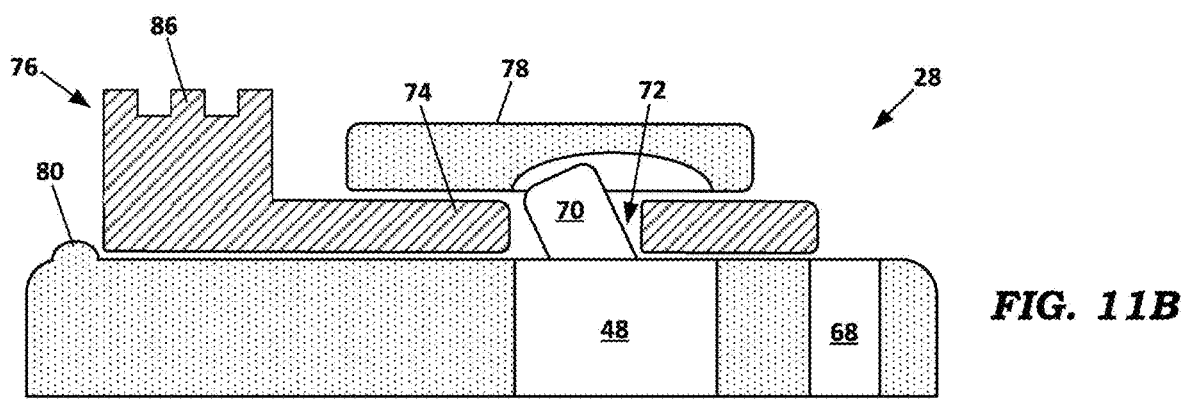
FIG. 11B

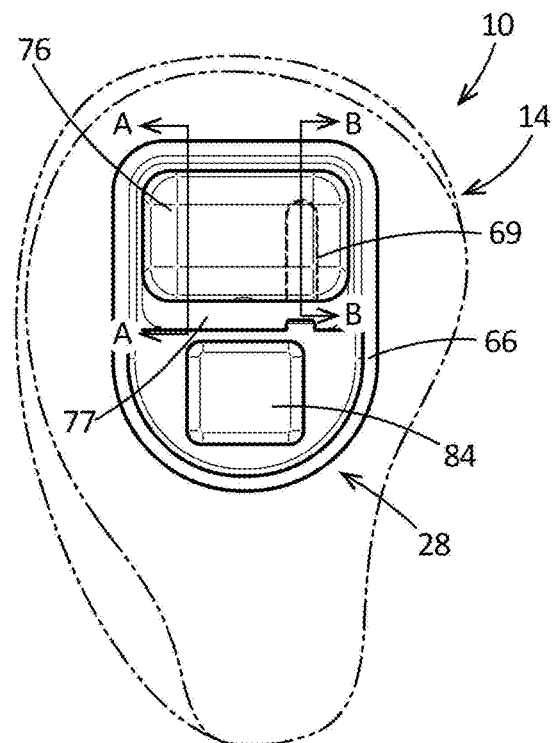
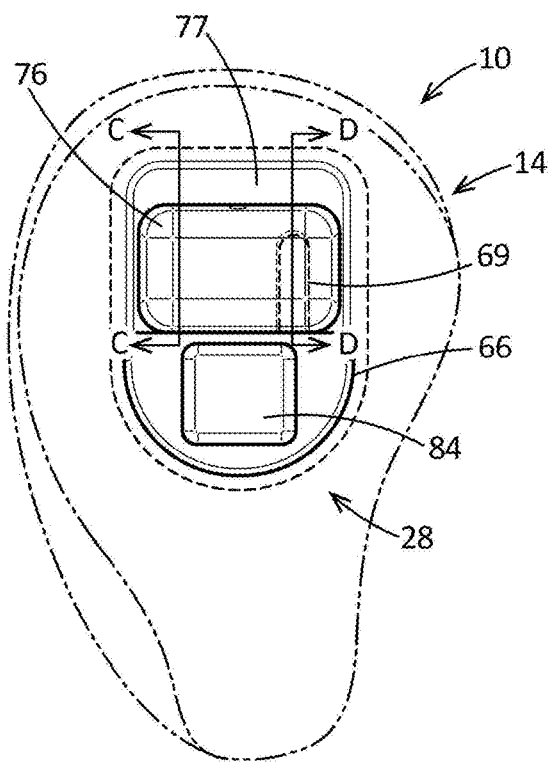
FIG. 17A  FIG. 17B
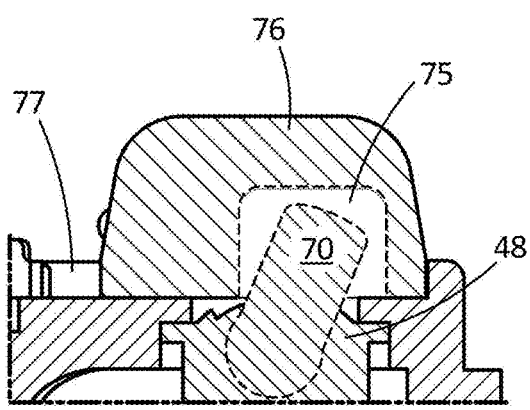
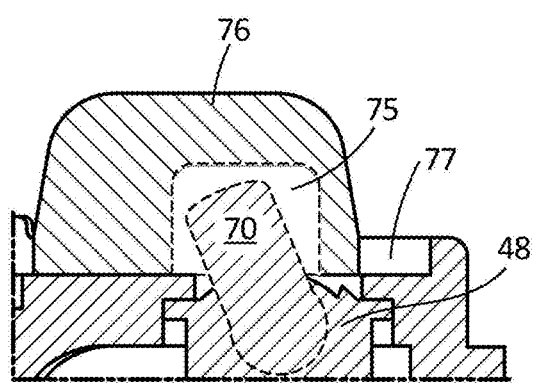
FIG. 18A
(Section A-A)
FIG. 18B
(Section C-C)

(Section B-B)

(Section D-D)

HEARING PROTECTION, NOISE MEASUREMENT AND COMMUNICATION SYSTEM

FIELD OF THE INVENTION

This invention relates to the field of electronic hearing protection. More particularly, this invention relates to a system for electronic hearing protection that features a custom-molded earplug and an electronic hearing device, where the electronic hearing device is switchable to permit sound to reach the user's ear or to prevent sound from reaching a user's ear.

BACKGROUND OF THE INVENTION

Hearing aids enhance a user's hearing by transmitting sound through a speaker assembly in the hearing aid and into the inner ear of the user. However, a problem exists if a user requires a hearing aid and also requires hearing protection, such as in military, industrial, hunting, or loud musical settings. Therefore, there is a need for a device that allows users to easily switch between hearing aid functionality and hearing protection functionality.

Previous hearing protection devices, such as earplugs, block out unwanted sound but provide no path for desired sound to travel. In other words, the user must take out the earplug out to hear the desired sound. Current hearing protection devices (such as described in U.S. Pat. No. 7,512,243B2 and US20210052429A1) provide hearing protection that involves manual operation of a movable structure to unblock some form of opening to allow sound through to the user's ear. These devices require manual sliding or rotation of the movable structure to alter the level of sound attenuation, but they do not provide for an electronic hearing device within the system. U.S. Pat. No. 10,045,133B2 describes a system that includes an electronic hearing device, but the electronic hearing device is external to the hearing protection system in a bulky and cumbersome orientation.

Thus, current hearing protection systems do not provide easy access to switch between quality sound filtering and adequate noise obstruction.

What is needed, therefore, is a device that allows users to easily switch between a hearing mode and a hearing protection mode, and that fits comfortably, securely, and discreetly in the user's ear.

SUMMARY OF THE INVENTION

The above and other needs are met by a hearing protection system comprising an earplug and an electronic hearing device. The earplug includes a first portion configured to be disposed in a user's outer ear and a second portion having a distal end configured for insertion into the user's ear canal. The first portion includes a recessed cavity having an inner profile. The second portion includes a sound tube having a first opening disposed within the recessed cavity of the first portion, and a second opening disposed at the distal end of the second portion.

The electronic hearing device is configured to be removably inserted into the recessed cavity of the earplug. The electronic hearing device includes a microphone for receiving external sound and generating an electrical sound signal based thereon, electronics that amplify the electrical sound signal, and a speaker assembly for generating sound based on the electrical sound signal. The electronics are operable to shut off sound amplification to protect the user when a loud noise is detected, and to resume sound amplification after the loud noise ends.

The electronic hearing device also includes a short-range communication interface for receiving a short-range communication signal that carries information.

The electronic hearing device also includes a housing in which the microphone assembly, speaker assembly, electronics and short-range communication interface are disposed. The housing has a front surface, a rear surface opposite the front surface, and a side surface disposed between the front and rear surfaces. A sound aperture is disposed in one or the surfaces of the housing for emitting the sound from the speaker assembly. The sound aperture is aligned with the first opening of the sound tube, thereby permitting the sound generated by the speaker assembly to propagate through the sound tube to the second opening.

In some embodiments, the electronics include fast compression programming that shuts off sound amplification when a loud noise is detected, and resumes amplification after the loud noise ends.

In some embodiments, the short-range communication interface comprises a nearfield communication (NFC) interface.

In some embodiments, the short-range communication interface is configured to receive the short-range communication signal carrying audio information.

In some embodiments, the hearing protection system includes a short-range transmitter disposed externally to the housing for transmitting the short-range communication signal to the short-range communication interface.

In some embodiments, the hearing protection system includes a long-range receiver disposed externally to the housing that is in electrical communication with the short-range transmitter. The long-range receiver is configured to receive wireless communications transmitted from a command center.

In some embodiments, the hearing protection system includes headgear configured to be worn by the user, such as a helmet, wherein the short-range transmitter and the long-range receiver are attached to or disposed within the headgear.

In some embodiments, at least a portion of the side surface of the housing extends outward from the recessed cavity in the first portion of the earplug, so that the side surface can be gripped by the user for pulling the housing out of the recessed cavity.

In some embodiments, the earplug is a custom earplug shaped to fit the shape of the user's ear canal based on an impression of the user's ear concha.

In some embodiments, the earplug is made of silicone.

In some embodiments, the electronic hearing device further comprises a switching device configured to be operated by the user to activate or deactivate the electronics.

In some embodiments, the electronic hearing device includes a switching device disposed within the housing and a programming button disposed adjacent the front surface of the housing. The programming button is operable to be pushed downward by the user to engage the switching device which causes the electronics to switch between multiple signal processing algorithms.

In some embodiments, pressing the programming button to engage the switching device controls the volume of sound provided by the electronics and speaker assembly.

In some embodiments, the inner profile of the recessed cavity substantially matches the side surface of the housing of the electronic hearing device.

In some embodiments, the electronic hearing device includes a protrusion extending outward from the side surface of the housing, and the inner profile of the recessed cavity includes a channel configured to receive the protrusion on the housing. This secures the housing within the recessed cavity while allowing the housing to be removed from the recessed cavity as a sufficient pulling force is applied to the housing.

In some embodiments, the digital signal processing is programmable to provide customized sound amplification according to a hearing profile of the user.

In some embodiments, the hearing protection system includes a noise dosimeter configured to be removably inserted into the recessed cavity of the earplug when the electronic hearing device has been removed therefrom. The noise dosimeter includes a first microphone, electronics, and an output interface. The first microphone receives sound and generates a first electrical sound signal based thereon. The electronics process the first electrical sound signal to generate first noise exposure measurement data related to a first dose of noise exposure over a period of time. The electronics include memory in which the first noise exposure measurement data are stored. The output interface is operable to download the first noise exposure measurement data to an external device.

The dosimeter includes a housing in which the first microphone, electronics, and output interface are disposed. The housing has a front surface, a rear surface opposite the front surface, and a side surface disposed between the front and rear surfaces. A first sound aperture is disposed in one of the surfaces of the housing through which the sound reaches the first microphone that is disposed adjacent to the first sound aperture.

In some embodiments, the first sound aperture is disposed in the front surface of the housing that is exposed to an external sound environment outside the user's outer ear when the earplug is inserted into the user's ear canal. In these embodiments, the first microphone receives sound from the external sound environment.

In some embodiments, the first sound aperture is disposed in the rear surface of the housing which is adjacent the first opening of the sound tube when the housing is disposed within the cavity of the earplug. In these embodiments, the first microphone receives sound that propagates through the sound tube from the user's ear canal when the earplug is inserted therein.

In some embodiments, the hearing protection system includes a second microphone that receives sound and generates a second electrical sound signal based thereon. The electronics process the second electrical sound signal to generate second noise exposure measurement data related to a second dose of noise exposure over the period of time. The housing includes a second sound aperture disposed in the rear surface of the housing which is adjacent the first opening of the sound tube when the housing is disposed within the cavity of the earplug. The second microphone is disposed adjacent the second sound aperture and receives sound that propagates through the sound tube from the user's ear canal when the earplug is inserted therein.

In some embodiments, the output interface comprises a Universal Serial Bus (USB) data interface or a wireless data interface.

In another aspect, embodiments of the invention are directed to a hearing protection kit comprising an earplug, an electronic hearing device, and a noise dosimeter. The earplug includes a first portion configured to be disposed in a user's outer ear and a second portion having a distal end configured for insertion into the user's ear canal. The first portion includes a recessed cavity having an inner profile. The second portion includes a sound tube having a first opening disposed within the recessed cavity of the first portion, and a second opening disposed at the distal end of the second portion.

The electronic hearing device is configured to be removably inserted into the recessed cavity of the earplug. The electronic hearing device includes a first microphone for receiving external sound and generating a first electrical sound signal based thereon, electronics that amplify the first electrical sound signal, and a speaker assembly for generating sound based on the first electrical sound signal. The electronics are operable to shut off sound amplification to protect the user when a loud noise is detected, and to resume sound amplification after the loud noise ends.

The electronic hearing device includes a first housing in which the first microphone assembly, speaker assembly, and first electronics are disposed. The first housing has a front surface, a rear surface opposite the front surface, and a side surface disposed between the front and rear surfaces. A first sound aperture is disposed in the rear surface or side surface for emitting the sound from the speaker assembly. The first sound aperture is aligned with the first opening of the sound tube, thereby permitting the sound generated by the speaker assembly to propagate through the sound tube to the second opening.

The noise dosimeter is configured to be removably inserted into the recessed cavity of the earplug when the electronic hearing device has been removed therefrom. The noise dosimeter includes a second microphone, second electronics, and an output interface. The second microphone receives sound and generates a second electrical sound signal based thereon. The second electronics process the second electrical sound signal to generate noise exposure measurement data related to a dose of noise exposure over a period of time. The second electronics include memory in which the noise exposure measurement data are stored. The output interface is operable to download the noise exposure measurement data to an external device.

The dosimeter includes a second housing in which the second microphone, second electronics, and the output interface are disposed. The second housing has a front surface, a rear surface opposite the front surface, and a side surface disposed between the front and rear surfaces. A second sound aperture is disposed in one of the surfaces of the second housing through which the sound reaches the second microphone that is disposed adjacent to the second sound aperture.

In yet another aspect, embodiments of the invention are directed to a method for using the hearing protection kit that includes the earplug, the electronic hearing device, and the noise dosimeter. A preferred embodiment of the method includes the following steps:

(a) inserting the noise dosimeter into the cavity of the earplug;
(b) inserting the earplug into the ear canal of the user;
(c) using the noise dosimeter to generate noise exposure measurement data during exposure to external noise;
(d) removing the earplug from the ear canal of the user;
(e) removing the noise dosimeter from the cavity of the earplug;
(f) downloading the noise exposure measurement data from the noise dosimeter;
(g) inserting the electronic hearing device into the cavity of the earplug;
(h) inserting the earplug into the ear canal of the user; and (i) using the electronic hearing device to protect the user during exposure to the external noise.

BRIEF DESCRIPTION OF THE DRAWINGS

Other embodiments of the invention will become apparent by reference to the detailed description in conjunction with the figures, wherein elements are not to scale so as to more clearly show the details, wherein like reference numbers indicate like elements throughout the several views, and wherein:

FIG. 9 depicts a functional block diagram of embodiments of the system;

FIG. 10 depicts a first switching device according to the second embodiment;

FIGS. 11A, 11B, 12A and 12B depict a cross-sectional side view of a slider and switch mechanism according to the second embodiment;

FIGS. 17A and 17B depict front views of the hearing protection system according to the third embodiment;

FIGS. 18A and 18B depict cross section views of a slider and switching device according to the third embodiment;

DETAILED DESCRIPTION

First Embodiment

Figure 1:
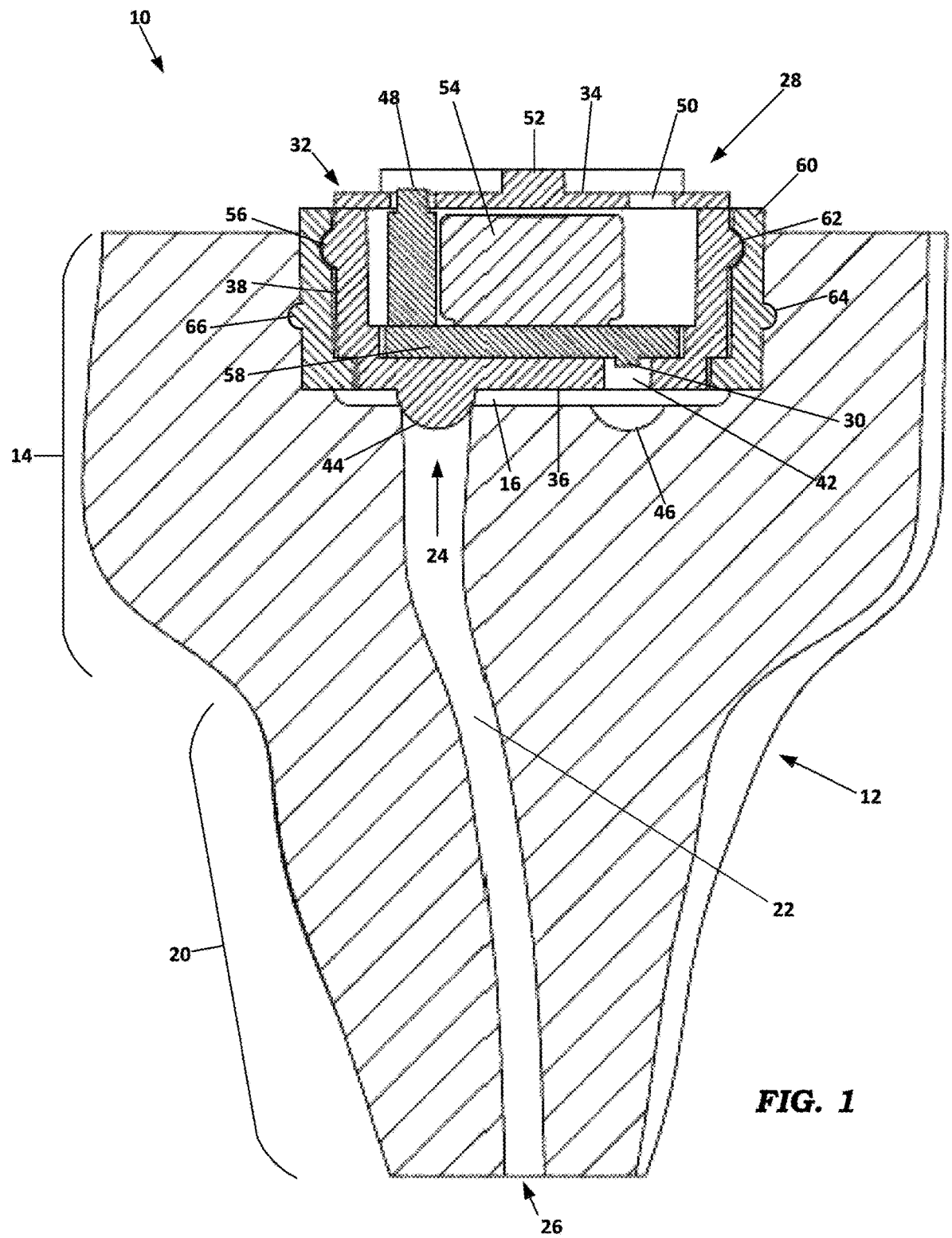
FIG. 1 depicts a cross-sectional side view of a hearing protection system in a hearing protection mode for blocking constant noise according to a first embodiment.
Figure 2:
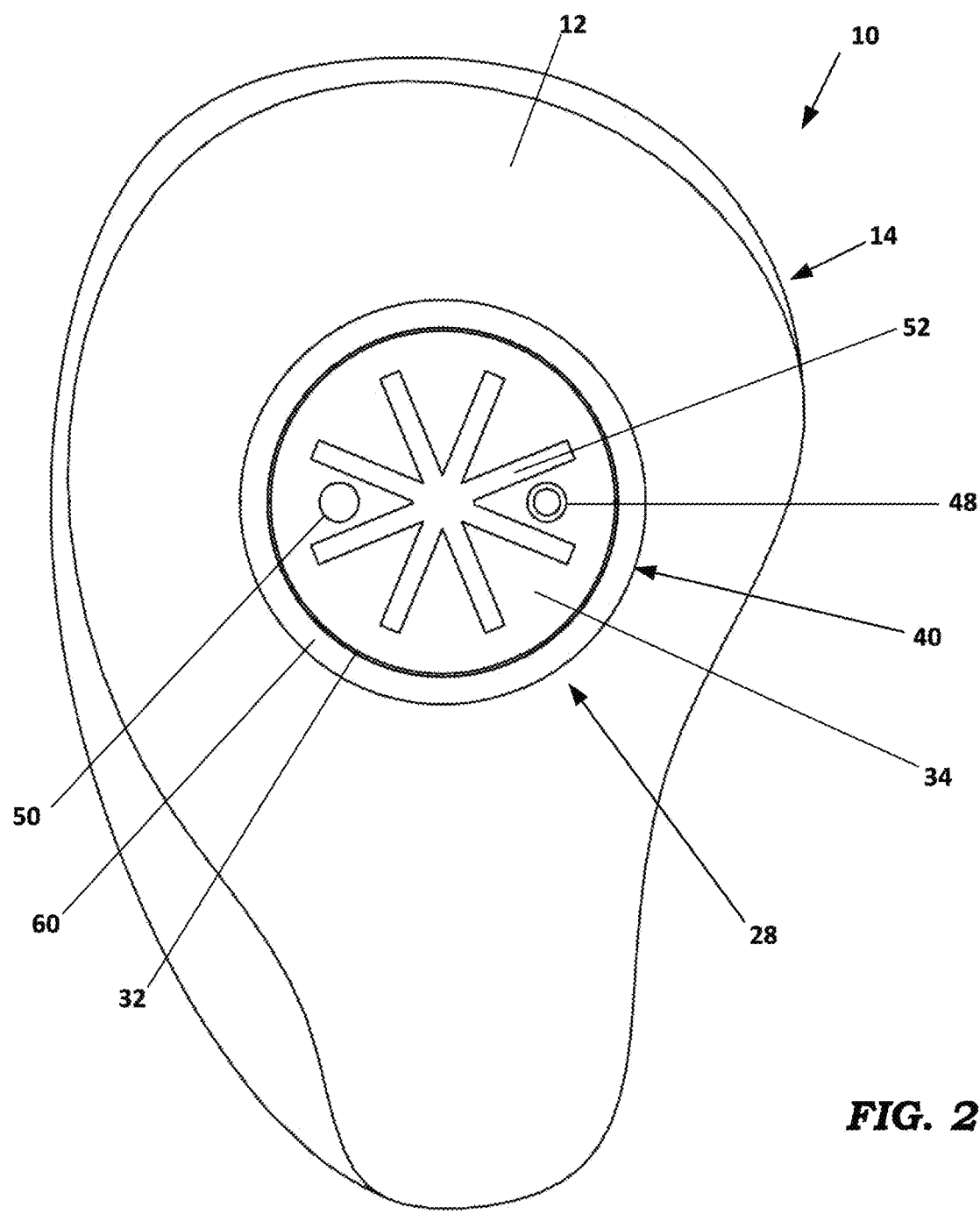
FIG. 2 depicts a front view of the hearing protection system according to the first embodiment.
Figure 3:
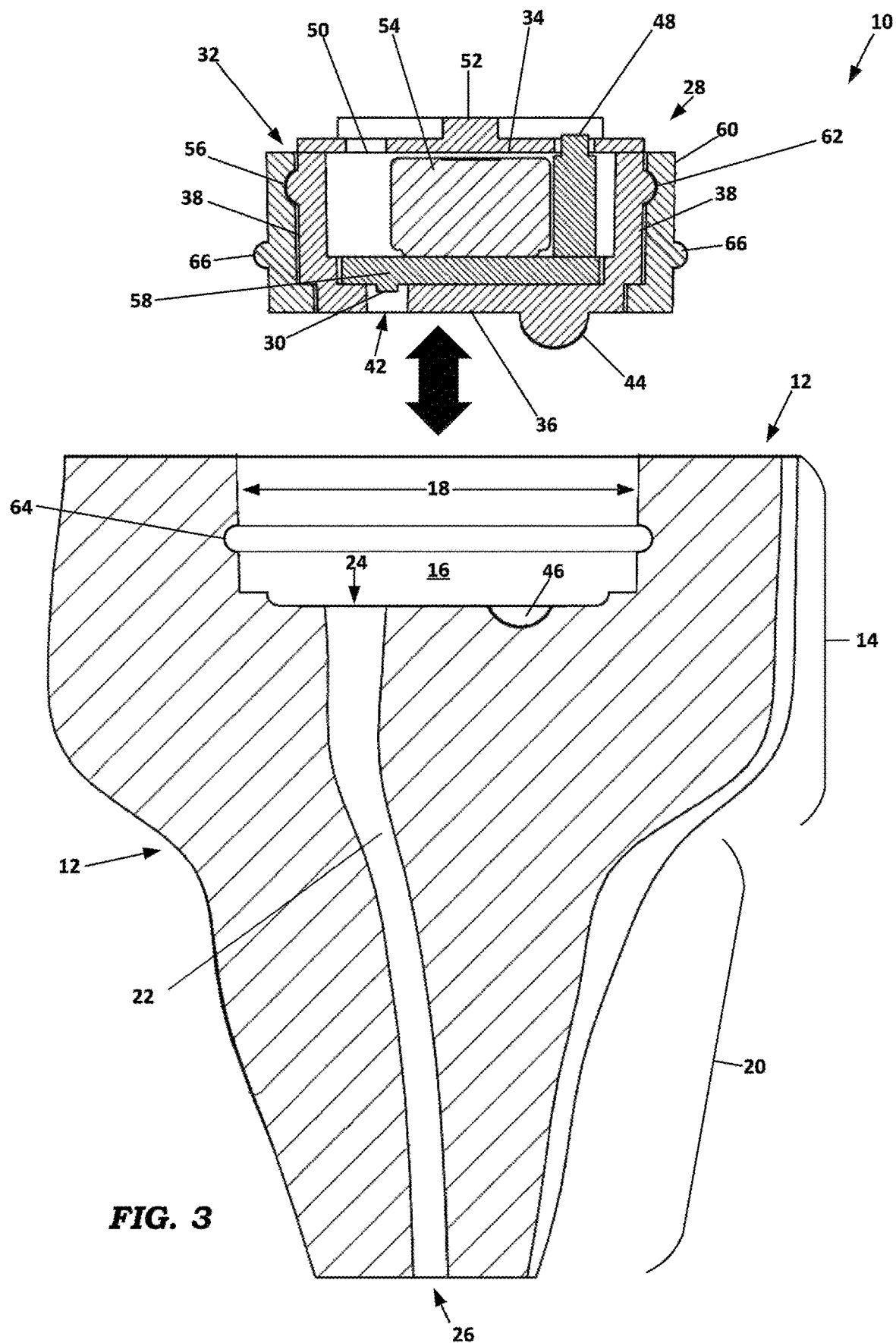
FIG. 3 depicts a cross-sectional side view of the hearing protection system in which an electronic hearing device portion of the system is removed from a custom earplug portion of the system according to the first embodiment.

FIGS. 1-4 and 9 depict a first embodiment of a custom electronic switchable hearing protection system 10. The hearing protection system 10 includes a custom earplug 12 having a first portion 14 and a second portion 20. The first portion 14, which is configured to fit in the user's outer ear, contains a recessed cavity 16 having an inner profile 18, as depicted in FIG. 3. The second portion 20 is configured to precisely fit into a user's ear canal. In a preferred embodiment, the custom earplug 12 is molded from silicone or other similarly compliant material using a mold having dimensions based on laser measurements or digital imaging of the user's ear canal. Alternatively, an impression of the ear canal may be made by casting.

In a preferred embodiment, the custom earplug 12 includes a sound tube 22 extending through the first portion 14 and the second portion 20 of the custom earplug 12. The sound tube includes a first opening 24 disposed within the recessed cavity 16 of the first portion 14 and a second opening 26 disposed at a distal end of the second portion 20. In some configurations of the system 10, the sound tube 22 allows sound to travel through the first opening 24 to the second opening 26 and then into the user's ear canal.

In a preferred embodiment, the hearing protection system 10 includes an electronic hearing device 28 that is configured to be inserted into the recessed cavity 16 of the custom earplug 12. The electronic hearing device 28 includes a microphone assembly 50 for receiving external sound, programmable electronics 58 for processing and amplifying the received sound according the user's preferences, a switching device 48, such as a pushbutton, rocker, or toggle switch, for controlling the electronics, a battery 54 for powering the electronics, and a speaker assembly 30 for generating the processed and amplified sound. The speaker assembly 30 may also be referred to as a receiver. The battery 54 may be replaceable or rechargeable.

The electronic hearing device 28 includes a housing 32 having a front surface 34 and an opposing rear surface 36. In the preferred embodiment, the housing 32 includes a generally cylindrical side surface 38 aligned perpendicular to the front and rear surfaces 34-36. A sound opening 42 is disposed in the rear surface 36 of the housing through which the sound generated by the speaker assembly 30 is emitted. In the preferred embodiment, the housing 32 of the electronic hearing device 28 is molded from a sturdy plastic, such as Photoplastic, or formed from metal. In some embodiments, the housing 32 is an acrylic material in which the electronic components are encased (potted) for protection from moisture.

The preferred embodiment of the system 10 includes a generally cylindrical outer ring 60 that surrounds the side surface 38 of the housing 32. As described in more detail hereinafter, the housing 32 is operable to rotate within the outer ring 60.

In a preferred embodiment, the electronics 58 incorporate programmable digital signal processing that provides for personalizing the electronic hearing device 28 to accommodate the hearing needs of the user based on user-selected algorithms. Examples of hearing assistance devices that incorporate such programmable digital signal processing are described in U.S. Pat. Nos. 7,974,716B2, 8,265,314B2, 8,284,968B2, 8,396,237B2, 8,077,890B2, 8,472,634B2, 8,811,642B2 and 9,031,272B2, the entire disclosures of which are incorporated herein by reference. In some embodiments, only one preset program is provided for amplification, in which case no user selection of programs is needed.

In a preferred embodiment, the switching device 48 is configured to allow the user to cycle the electronic hearing device 28 between different settings, including at least two different user-selected signal processing algorithms. In some embodiments, the switching device 48 is also configured to power-on or power-off the electronic hearing device 28. In some embodiments, the switching device 48 also can be used to adjust the volume of the sound generated by the speaker assembly 30.

In a preferred embodiment, the hearing protection system 10 includes a grip portion 52 extending outward from the front surface 34 of the housing 32. The grip portion 52 is configured to be gripped by the user for rotating the housing 32 within the recessed cavity 16. In some embodiments, the grip portion 52 is comprised of a rotatable circular structure with at least one tab to be gripped by the user. In an alternative embodiment, the grip portion 52 comprises a knurled knob that extends outward from the front surface 34.

As shown in FIG. 2, the outer ring 60 has an outer profile 40 that is configured to correspond to the inner profile 18 of the recessed cavity 16 of the custom earplug 12. The outer profile 40 and inner profile 18 are configured so that the electronic hearing device 28 is held securely within the custom earplug 12, but also to allow the electronic hearing device 28 to be easily removed and replaced by the user, such as when the charge on the battery 54 is depleted. In a preferred embodiment, the friction force between the outer profile 40 and the inner profile 18 is larger than the friction force between the outer ring 60 and the housing 32, so as to allow the user to rotate the housing 32 within the outer ring 60 without causing rotation of the outer ring 60 within the recessed cavity 16.

In a preferred embodiment, at least one annular retainer protrusion 66 extends outward from the cylindrical side surface 38 of the outer ring 60. The retainer protrusion 66 is received into a corresponding annular retainer channel 64 in the inner surface of the recessed cavity 16. This arrangement ensures that the electronic hearing device 28 is retained within the recessed cavity 16 until a user intentionally removes the electronic hearing device 28 from the cavity 16 by applying a sufficient pulling force.

Also in a preferred embodiment, at least one annular protrusion 56 extends outward from the cylindrical side surface 38 of the housing 32. The protrusion 56 is received into a corresponding annular channel 62 in the inner surface of the outer ring 60. This arrangement keeps the housing 32 locked into the outer ring 60, while allowing the housing 32 to rotate within outer ring 60 when a rotational force is applied to the housing 32.

In a preferred embodiment, the housing 32 is configured to be rotatable within the outer ring 60 between multiple positions, including a first position and a second position. In the first position, the sound opening 42 aligns with the first opening 24 of the sound tube 22, thereby permitting the sound generated by the speaker assembly 30 to propagate through the sound tube 22 to the second opening 26. In the second position, the rear surface 36 of the housing 32 at least partially blocks the first opening 24 of the sound tube 22, thereby at least partially preventing sound from entering the sound tube 22. In the preferred embodiment, the housing 32 is configured to rotate 180 degrees from the first position to the second position. However, it will be appreciated that the first and second positions could be rotationally spaced apart at other angles.

In some embodiments, the electronic hearing device 28 includes a protrusion 44 extending outward from the rear surface 36 of the housing 32 and spaced apart from the sound opening 42 of the housing 32. The protrusion 44 is configured to align with and at least partially block the first opening 24 of the sound tube 22 when the housing 32 is rotated to the second position. In some embodiments, an indentation 46 is disposed within the surface of the recessed cavity 16 that engages the rear surface 36 of the housing 32. The indentation 46 is configured to receive the protrusion 44 at least partially when the housing 32 is in the first position.

In some embodiments, when a loud noise is detected by the microphone 50, the programmable electronics 58 of the electronic hearing device 28 utilizes a fast compression algorithm to quickly attenuate the corresponding sound provided to the speaker assembly 30 so that the sound that reaches the user's ear canal will not cause hearing damage. The fast compression algorithm preferably has a fast-acting attack time of between 0.5 msec and 20 msec to implement the attenuation. In a preferred embodiment, the programmable electronics 58 remove the attenuation when the excessive loud noise ceases, thereby returning to normal operation. The attack time is preferably a programmable preset value.

Figure 4:
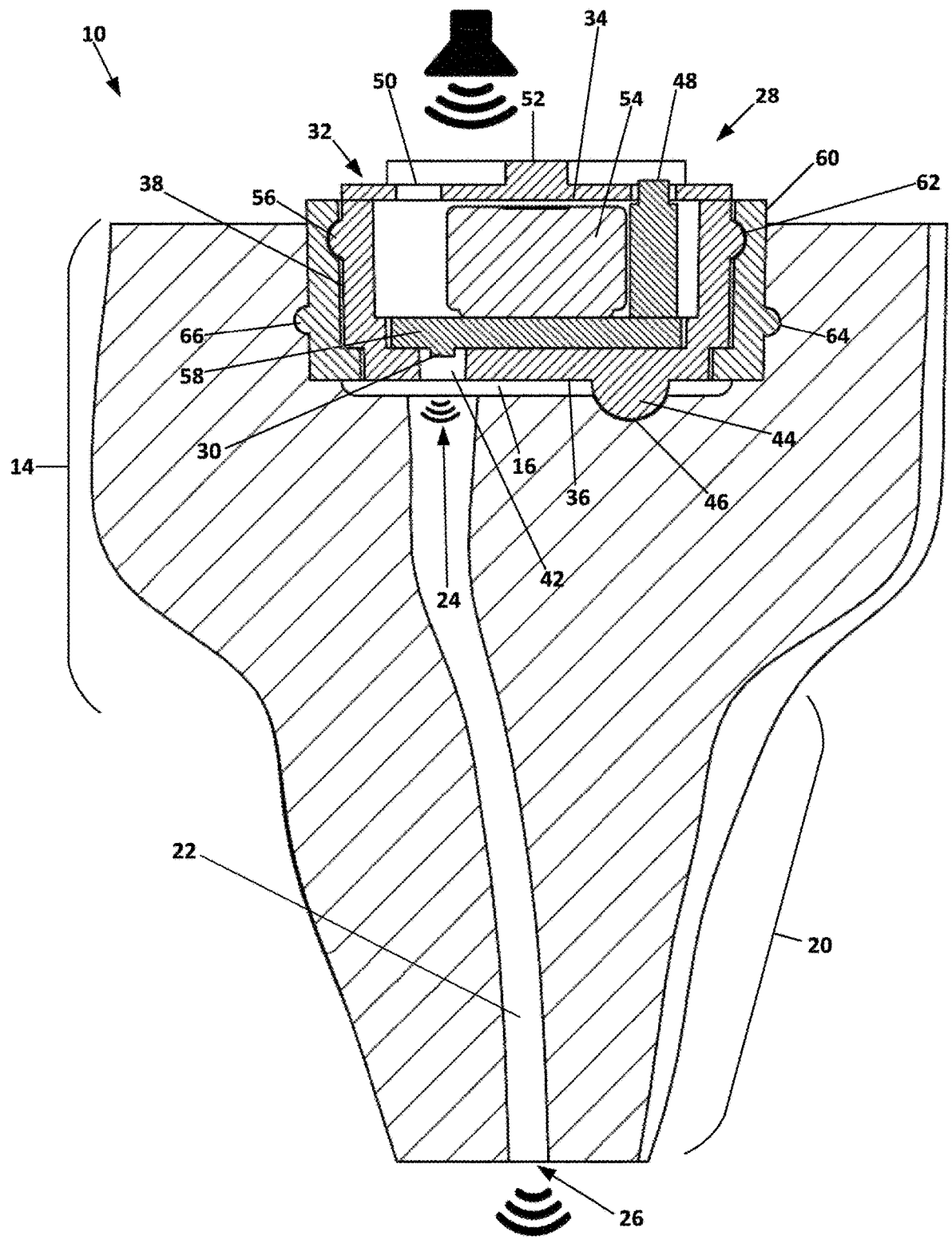
FIG. 4 depicts a cross-sectional side view of the hearing protection system in an active hearing mode according to the first embodiment.
Figure 5A:
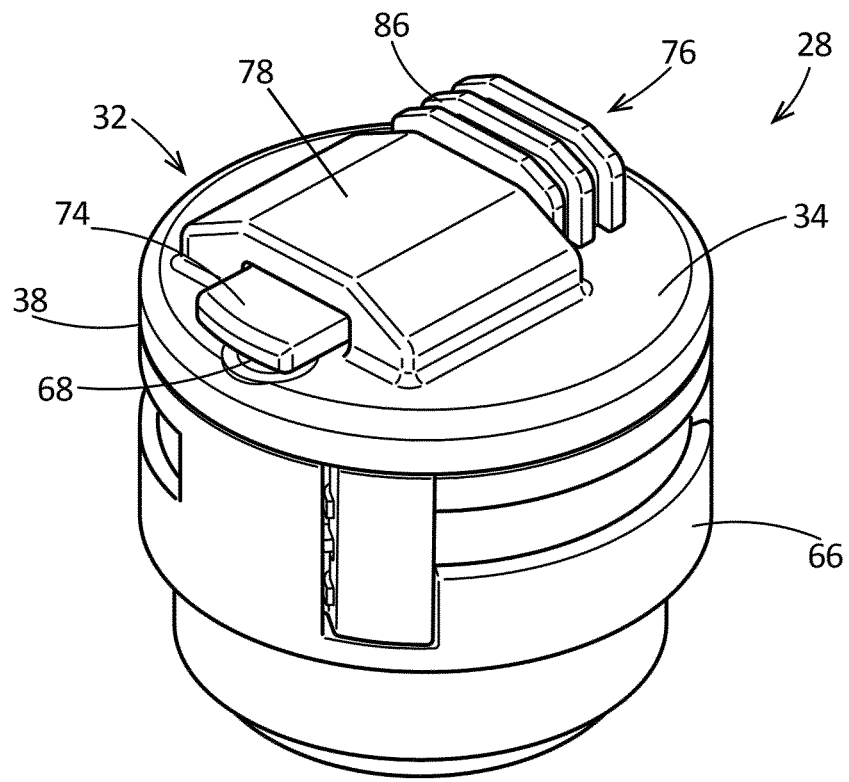
FIGS. 5A, 5B, 5C, 5D, 5E, 5F, 5G, 5H, 5I and 5J depict an electronic hearing device of a hearing protection system according to a second embodiment of the invention.
Figure 5B:
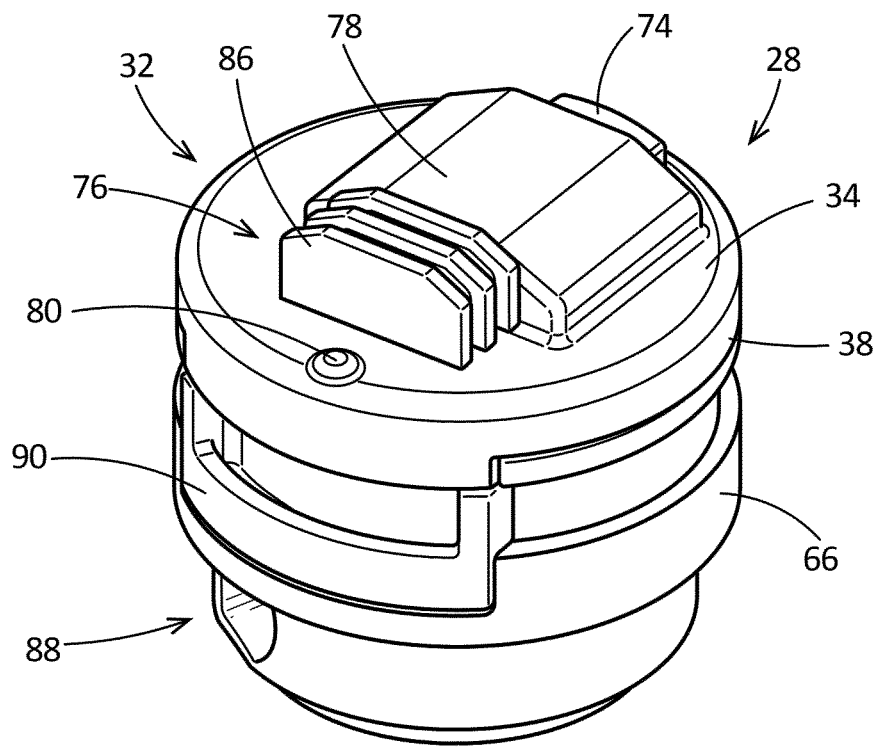
Figure 5C:
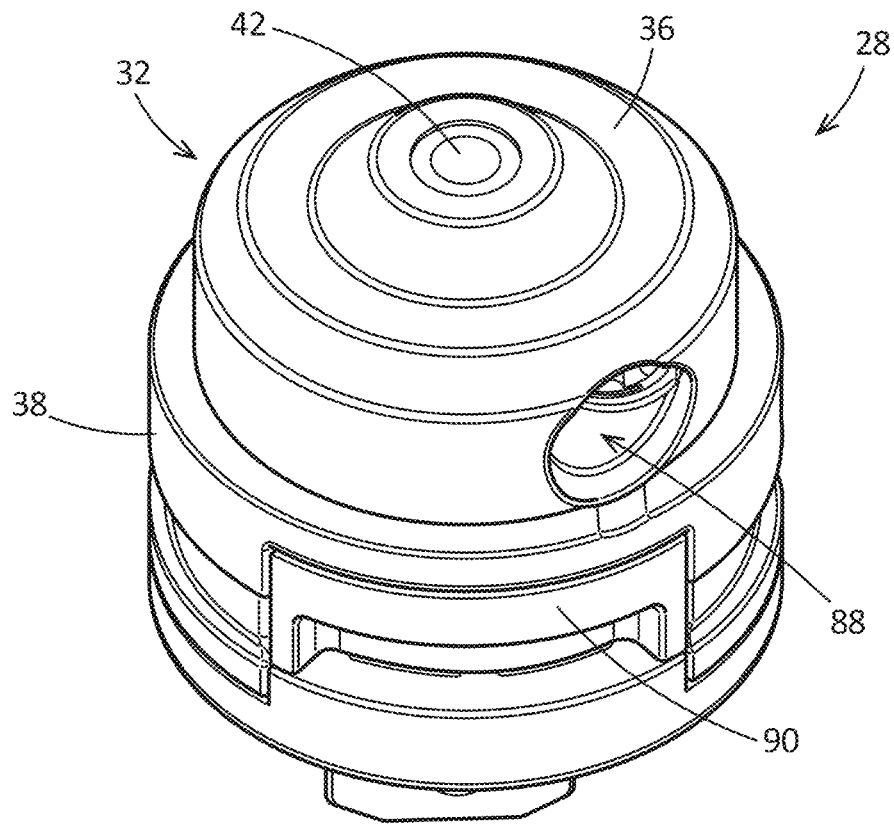
Figure 5D:
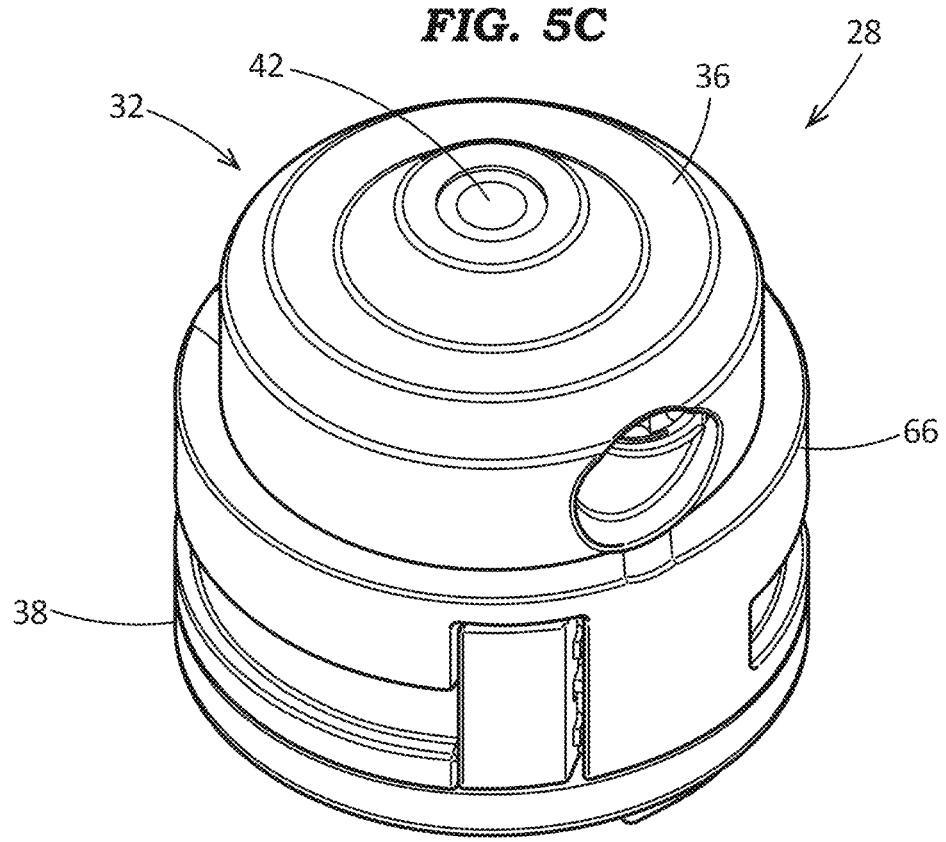
Figure 5E:
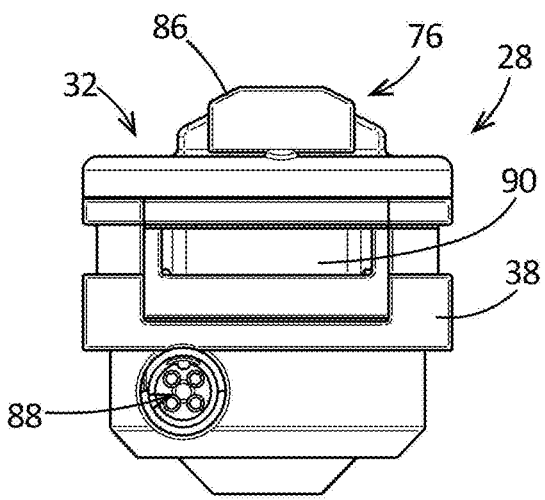
Figure 5F:
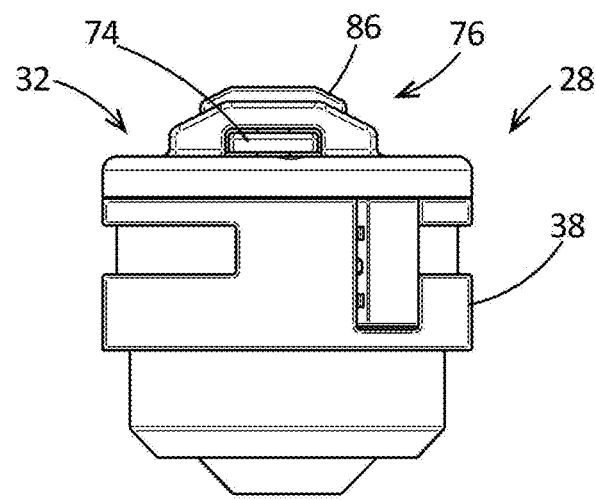
Figure 5G:
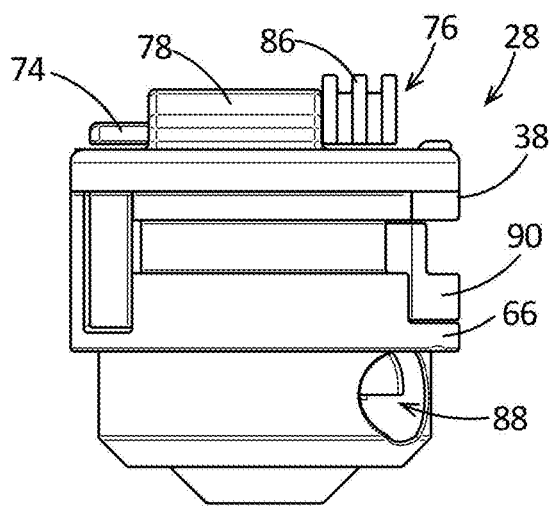
Figure 5H:
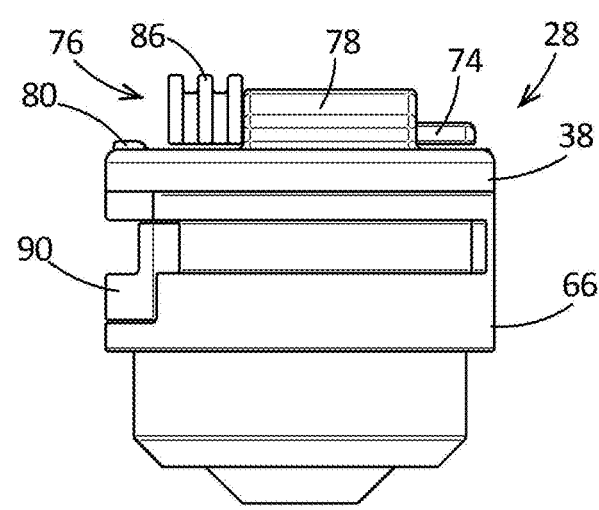
Figure 5I:
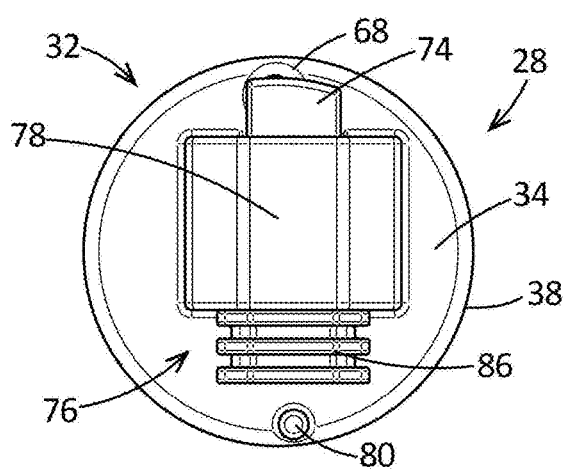
Figure 5J:
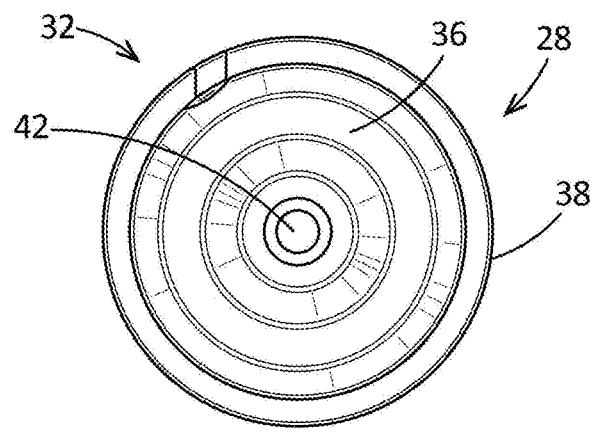

FIG. 4 depicts a preferred embodiment of the hearing protection system 10 in the active hearing aid mode. The external sound is received through the microphone 50 which generates an electrical signal that is provided to the programmable electronics 58 of the electronic hearing device 28. The programmable electronics 58 process and amplify the sound signal, which is provided to the speaker assembly 30 to generate audible sound at the sound opening 42. The sound from the speaker assembly 30 propagates into the first opening 24 of the sound tube 22 and through the sound tube 22 to the second opening 26 and into the user's ear canal.

Second Embodiment

Figure 6:
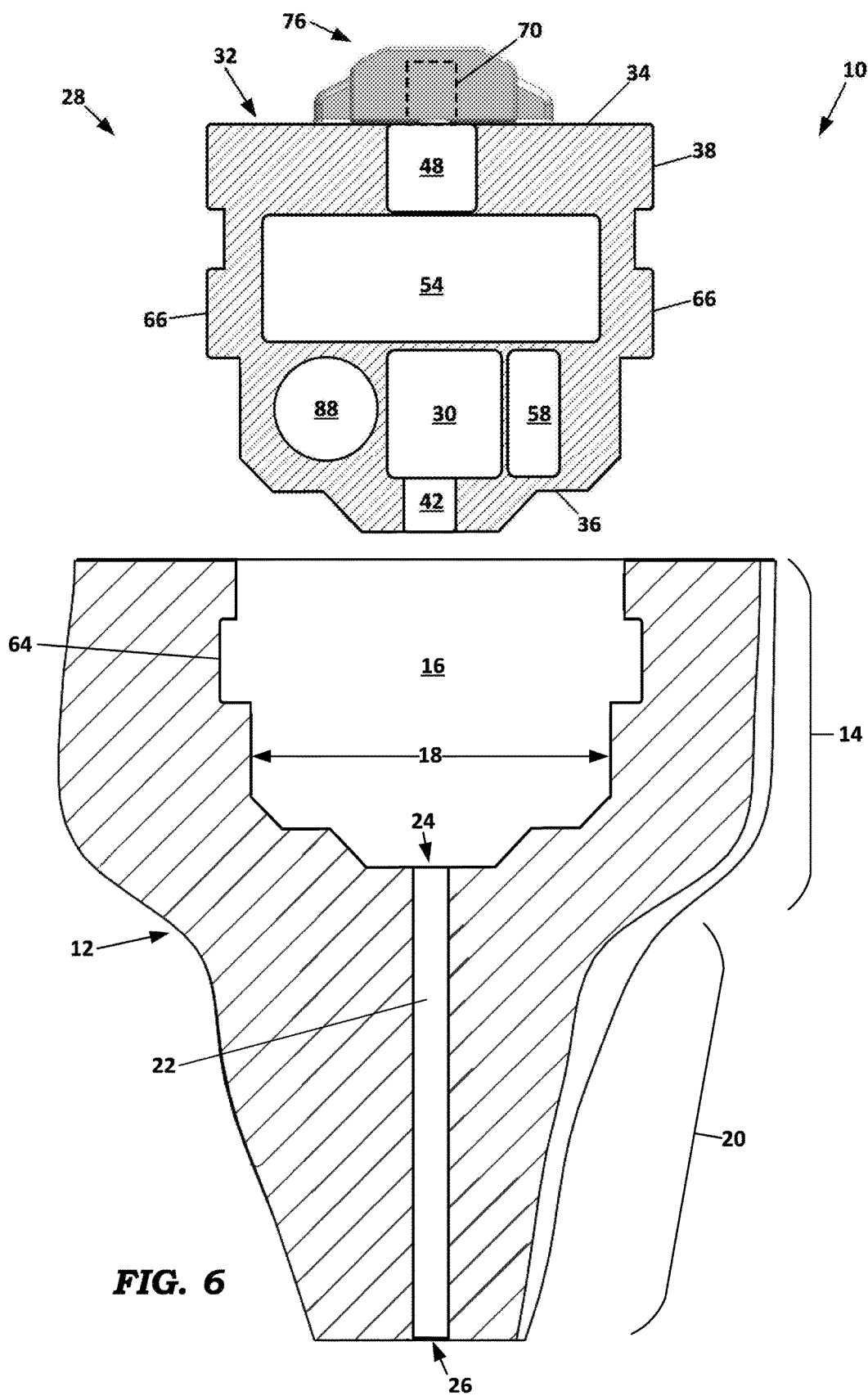
FIG. 6 depicts a cross-sectional side view of a hearing protection system in which the electronic hearing device is removed from the custom earplug according to the second embodiment.
Figure 7:
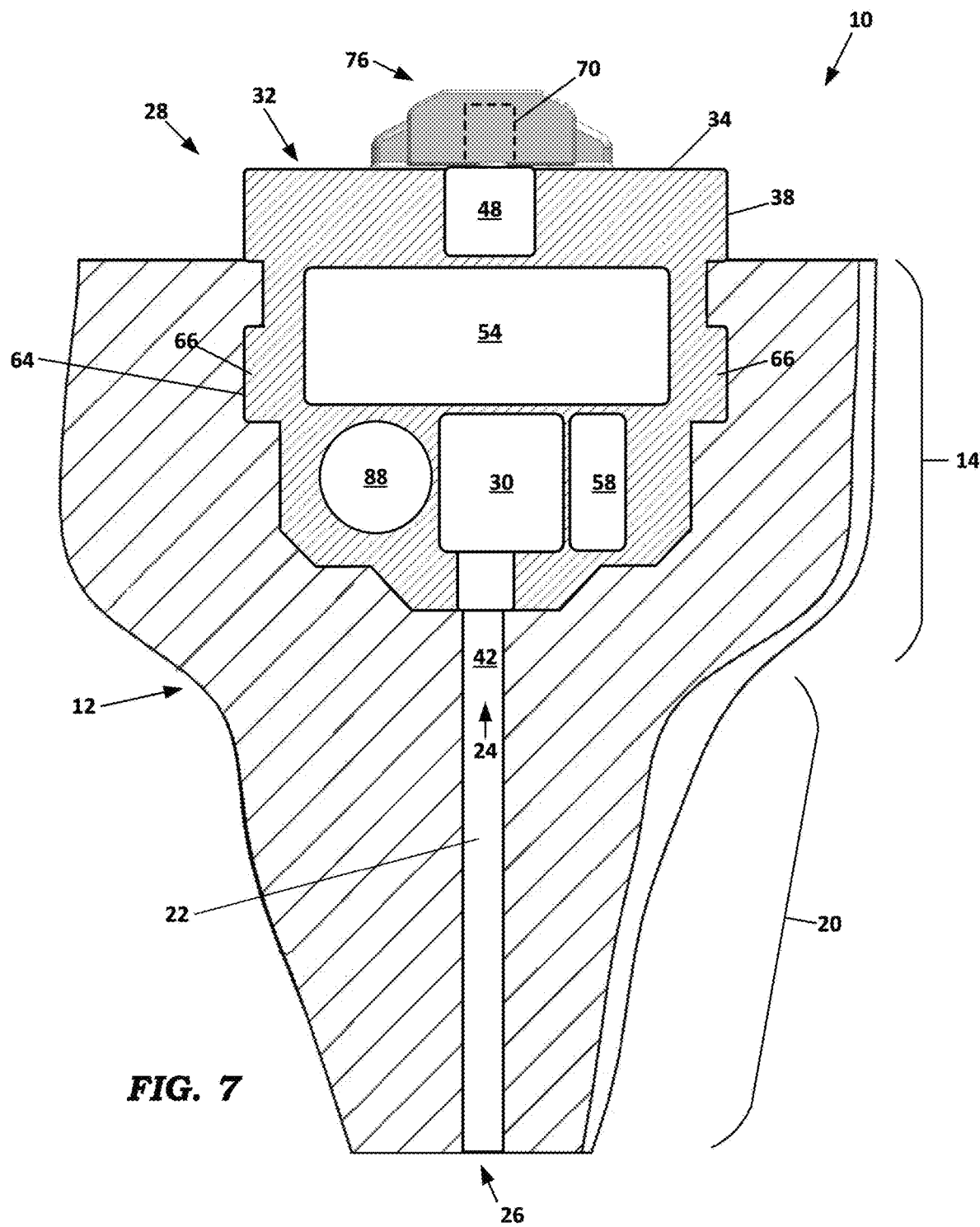
FIG. 7 depicts a cross-sectional side view of the hearing protection system in which the electronic hearing device is inserted into the custom earplug according to the second embodiment.
Figure 8:
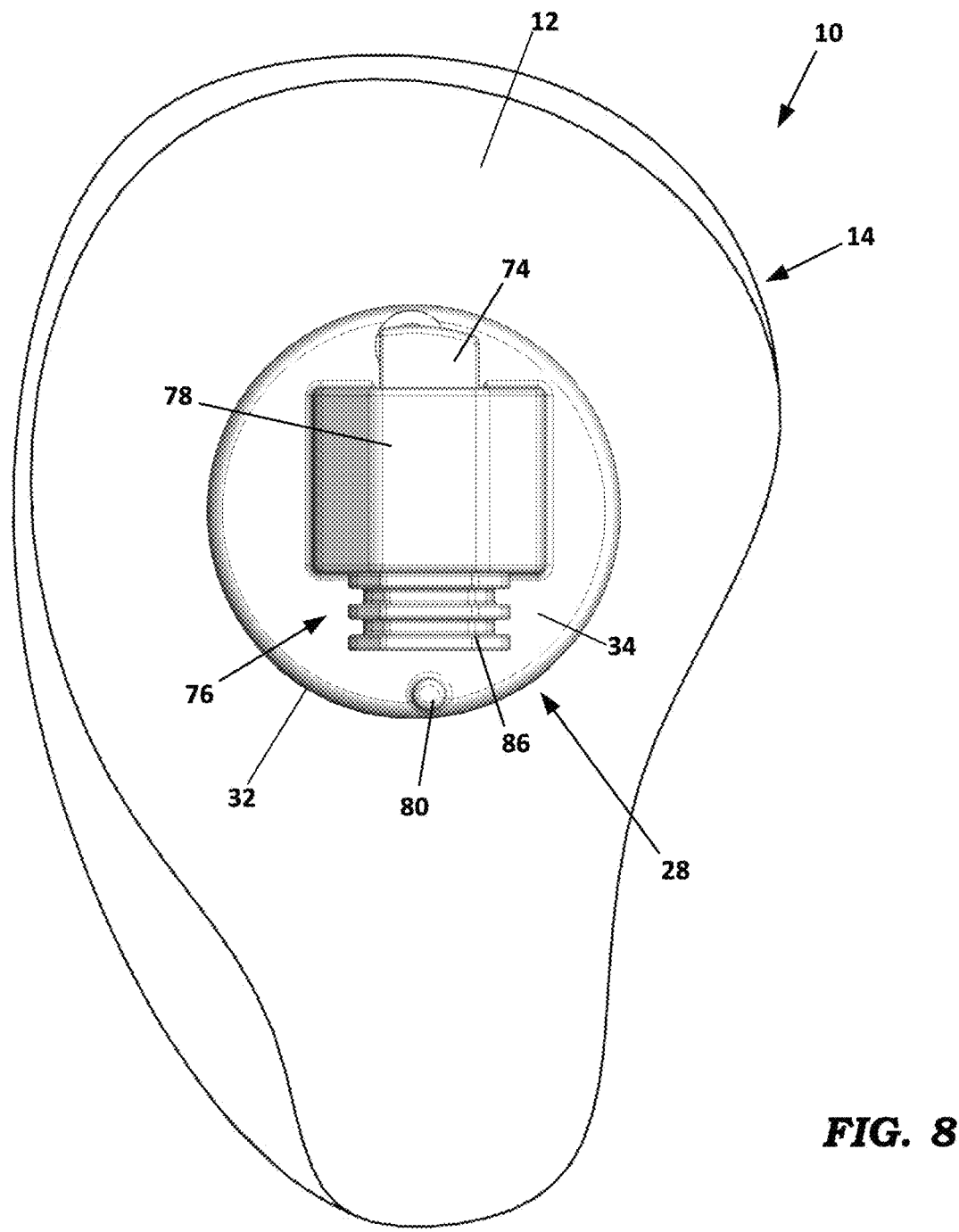
FIG. 8 depicts a front view of the hearing protection system according to the second embodiment.

FIGS. 5A-5J, 6-10, 11A-11B, and 12A-12C depict a second embodiment of a custom electronic switchable hearing protection system 10. As shown in FIGS. 6 and 7, the hearing protection system 10 includes a custom earplug 12 having a first portion 14 and a second portion 20. The first portion 14, which is configured to fit in the user's outer ear, contains a recessed cavity 16 having an inner profile 18. The second portion 20 is configured to precisely fit into a user's ear canal. In a preferred embodiment, the custom earplug 12 is molded from a compliant material, such as silicone, using a mold having dimensions based on laser measurements or digital imaging of the user's ear canal. Alternatively, an impression of the ear canal may be made by casting.

In a preferred embodiment, the custom earplug 12 includes a sound tube 22 extending through the first portion 14 and the second portion 20 of the custom earplug 12. The sound tube includes a first opening 24 disposed within the recessed cavity 16 of the first portion 14 and a second opening 26 disposed at a distal end of the second portion 20.

In some configurations of the system 10, the sound tube 22 allows sound to travel through the first opening 24 to the second opening 26 and then into the user's ear canal.

In a preferred embodiment, the hearing protection system 10 includes an electronic hearing device 28 that is configured to be inserted into the recessed cavity 16 of the custom earplug 12. As shown in FIG. 9, the electronic hearing device 28 includes a microphone assembly 50 for receiving external sound, programmable electronics 58 for processing and amplifying the received sound according the user's preferences, first and second switching devices 48 and 82, such as pushbutton, rocker, or toggle switches, for controlling the electronics 58, a battery 54 for powering the electronics 58, and a speaker assembly 30 for generating the processed and amplified sound. The battery 54 may be replaceable or rechargeable.

The electronic hearing device 28 includes a housing 32 having a front surface 34 and an opposing rear surface 36. In the preferred embodiment, the housing 32 includes a generally cylindrical side surface 38 disposed between the front and rear surfaces 34 and 36. A microphone aperture 68 is disposed in the upper surface 34 of the housing 32 through which sound travels to the microphone assembly 50. A sound opening 42 is disposed in the rear surface 36 of the housing through which the sound generated by the speaker assembly 30 is emitted. In the preferred embodiment, the housing 32 of the electronic hearing device 28 is molded from a sturdy plastic, such as Photoplastic, or formed from metal. In some embodiments, the housing 32 is an acrylic material in which the electronic components are encased (potted) for protection from moisture.

In some preferred embodiments, the electronics 58 incorporate programmable digital signal processing that provides for personalizing the electronic hearing device 28 to accommodate the hearing needs of the user based on a preloaded algorithm or a user-selected algorithm. Examples of hearing assistance devices that incorporate programmable digital signal processing are described in U.S. Pat. Nos. 7,974,716B2, 8,265,314B2, 8,284,968B2, 8,396,237B2, 8,077,890B2, 8,472,634B2, 8,811,642B2 and 9,031,272B2, the entire disclosures of which are incorporated herein by reference. In some embodiments, a single preset program is loaded on the device 28 that provides a normal level of amplification for a typical user who has no hearing loss, in which case no user selection of programs is needed. In some embodiments, the single preset program is optimized for the individual user's hearing profile.

In preferred embodiments, when a loud noise is detected by the microphone assembly 50, the programmable electronics 58 of the electronic hearing device 28 utilize a fast compression algorithm to quickly attenuate the corresponding sound provided to the speaker assembly 30 to prevent hearing damage. The fast compression algorithm preferably has a fast-acting attack time of between 0.5 msec and 20 msec to implement the attenuation. In a preferred embodiment, the programmable electronics 58 remove the attenuation when the excessively loud noise ceases, thereby returning to normal operation. The attack time is preferably a programmable preset value.

As shown in FIGS. 5A, 5B, 5E-5I, and 11A-11B, a preferred embodiment of the electronic hearing device 28 incorporates a slider 76 that includes a slider handle 86, a slider blade 74, and a slider aperture 72 in the slider blade 74. The slider 76 is operable to slide relative to the front surface 34 of the housing 32 of the electronic hearing device 28, and the slider blade 74 is operable to slide within a slider shroud 78 attached to the front surface 34. The slider blade 74 includes a slider aperture 72 that receives a toggle lever 70 of the first switching device 48. In a preferred embodiment, the slider handle 86 has a slotted engagement surface that a user may engage with a fingertip to move the slider 76 between a first position depicted in FIG. 11A and a second position depicted in FIG. 11B. The movement of the slider 76 is limited by engagement of the slider handle 86 with a stop 80 extending from the front surface 34 (second position limit) and with an edge of the slider shroud 78 (first position limit). As shown in the various figures, the slider shroud 78 is large enough to substantially cover the slider aperture 72 and the toggle lever 70 throughout the range of movement of the slider 76, thereby preventing entry of particulate matter that could damage the first switching device 48.

As shown in the cross section views of FIGS. 11A and 11B, when the slider 76 is moved to the first position, the toggle lever 70 of the first switching device 48 is moved to a first switch position, and when the slider 76 is moved to the second position, the toggle lever 70 of the first switching device 48 is moved to a second switch position. When the first switching device 48 is in the first switch position, the electronics 58 are turned off or otherwise deactivated, such that sounds received by the microphone assembly 50 are not amplified and provided to the speaker assembly 30. When the first switching device 48 is in the second switch position, the electronics 58 are activated, such that sounds received by the microphone assembly 50 are amplified and provided to the speaker assembly 30.

Also, when the slider 76 is in the first position, the microphone aperture 68 is covered by the slider blade 74. This prevents dust and moisture from entering the aperture 68 when the microphone assembly 50 is not in use. When the slider 76 is in the second position, the microphone aperture 68 is uncovered, thereby allowing sound to enter the microphone aperture 68 when the microphone assembly 50 is in use.

Figure 12A:
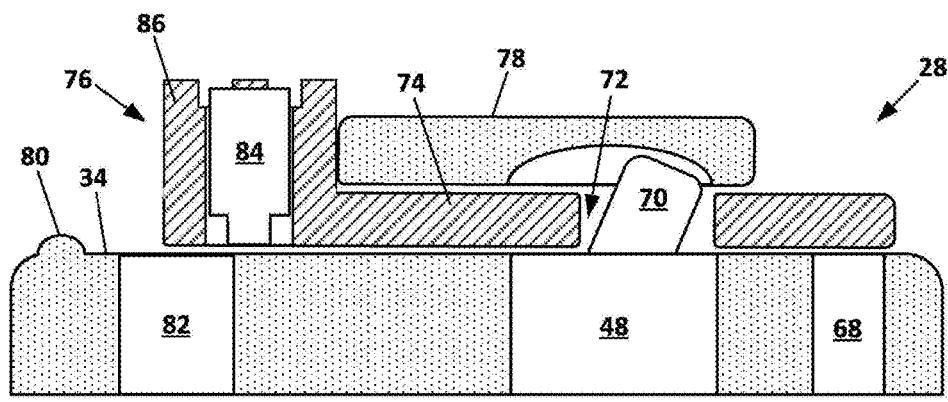
Figure 12B:
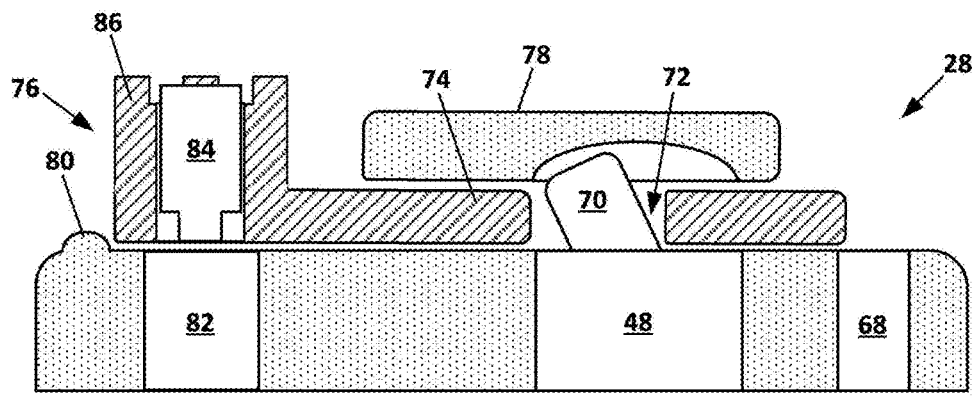
Figure 12C:
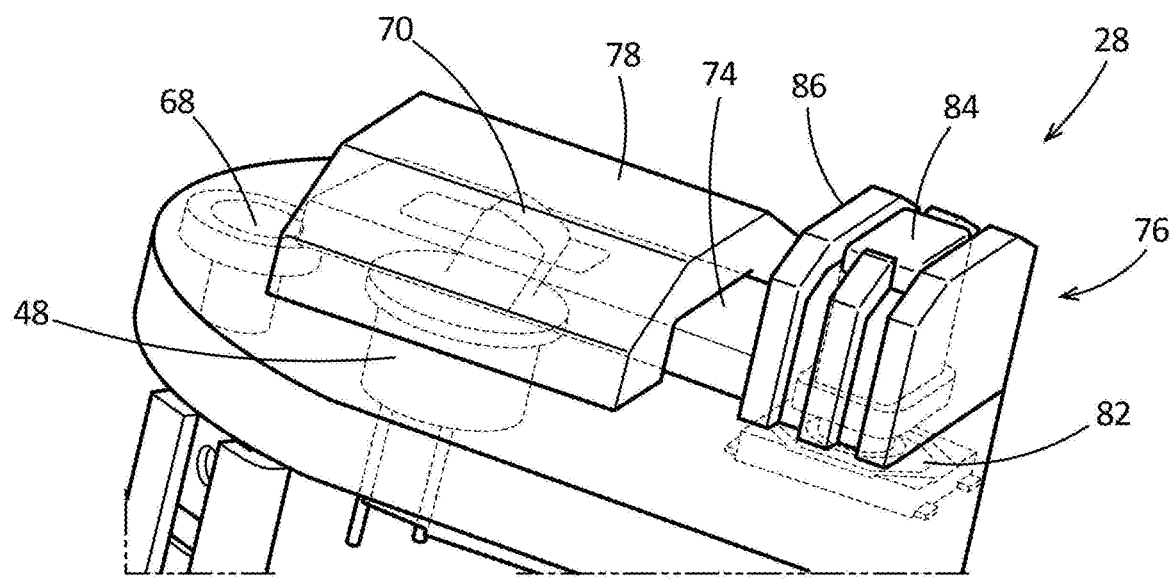
FIG. 12C depicts a perspective cutaway view of the slider and switch mechanism according to the second embodiment.

As shown in FIGS. 12A-12C, a preferred embodiment of the electronic hearing device 28 includes a programming button 84 integrated into an aperture in the slider handle 86. The programming button 84 is biased toward the engagement surface of the slider handle, such as by a leaf spring or other biasing mechanism integrated into the slider handle 86. When the slider 76 is in the second position as shown in FIG. 12B, the programming button 84 is operable to be pushed downward by a user to press a second switching device 82 disposed within the housing 32 of the electronic hearing device 28. Pressing the second switching device 82 allows the user to switch between and select different settings, including at least two different signal processing algorithms/programs stored in the electronics 58. The second switching device 82 may also be used to control the volume of the amplification provided by the electronics 58 and speaker assembly 30.

As shown in FIGS. 5B, 5C, 5E, 5G, 6 and 7, embodiments of the electronic hearing device 28 include a programming port 88 that is operable to receive a programming connector to allow for programming of the electronics 58 using an external computing device.

Figure 13:
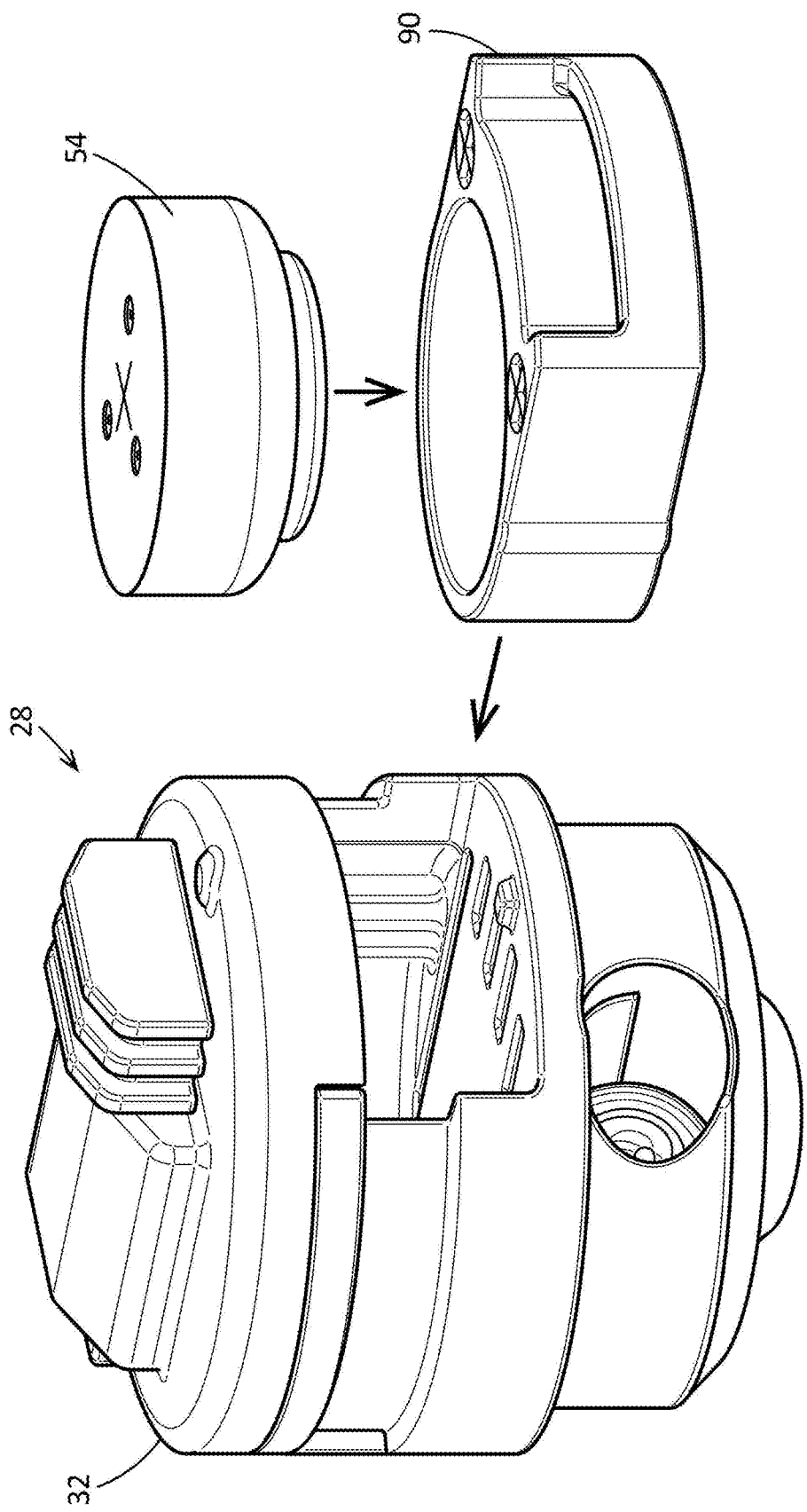
FIG. 13 depicts a battery drawer and battery removed from an electronic hearing device according to the second embodiment.
Figure 14A:
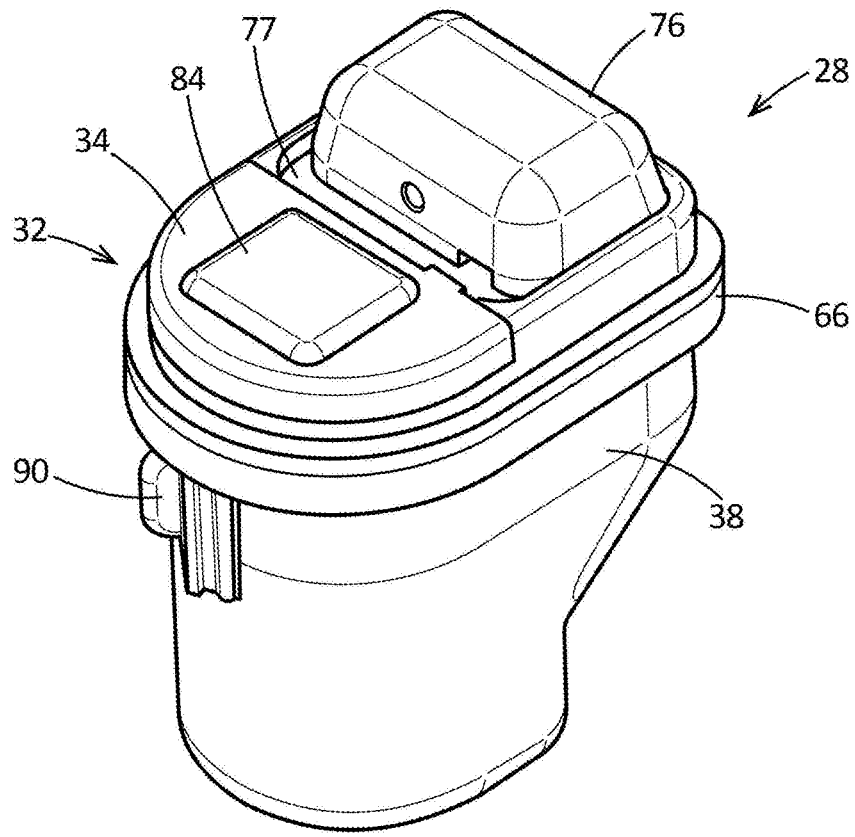
FIGS. 14A, 14B, 14C, 14D, 14E, 14F, 14G, 14H, 14I and 14J depict an electronic hearing device of a hearing protection system according to a third embodiment of the invention.
Figure 14B:
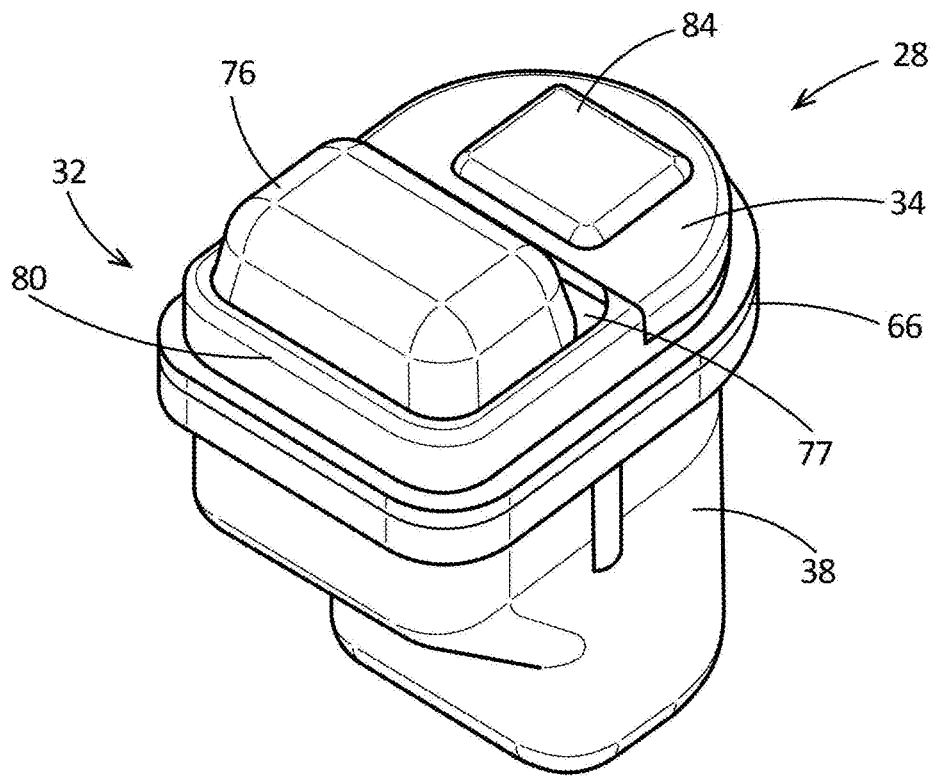
Figure 14C:
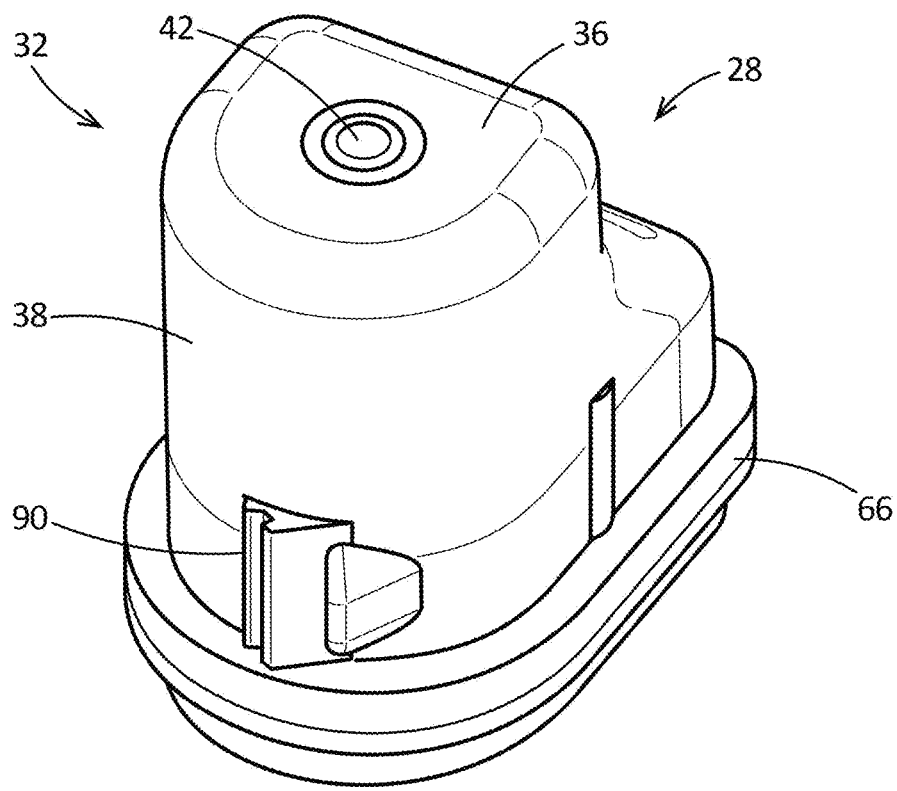
Figure 14D:
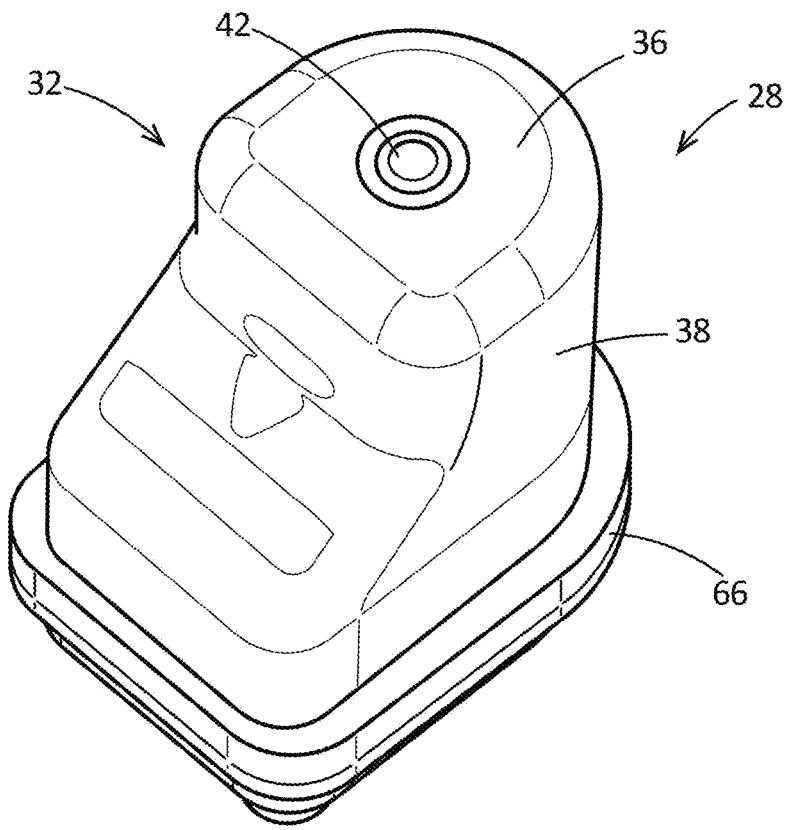
Figure 14E:
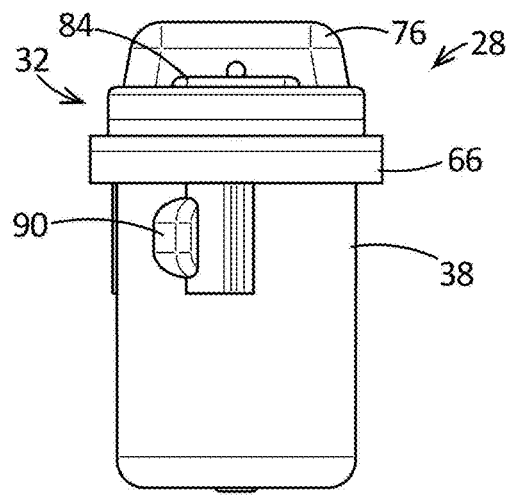
Figure 14F:
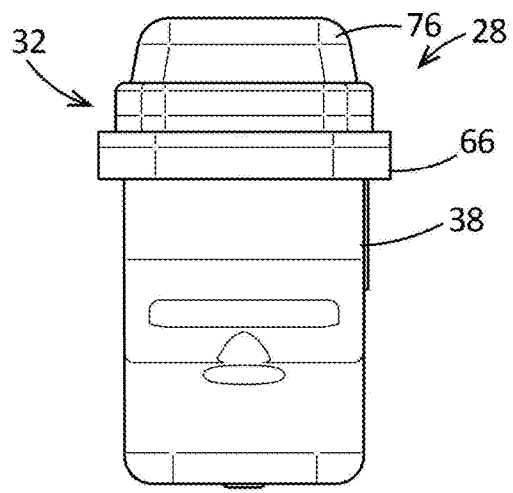
Figure 14G:
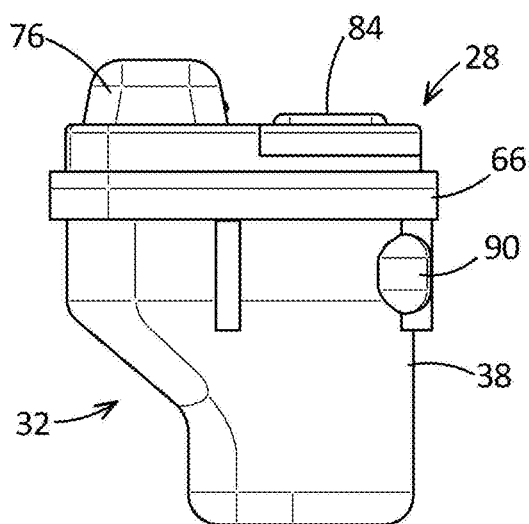
Figure 14H:
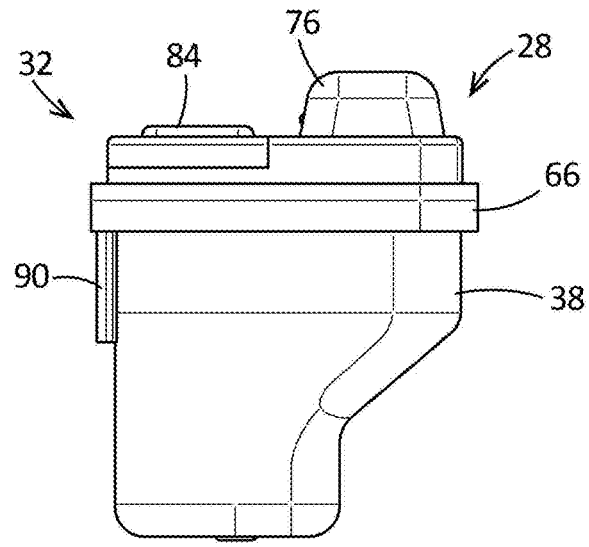
Figure 14I:
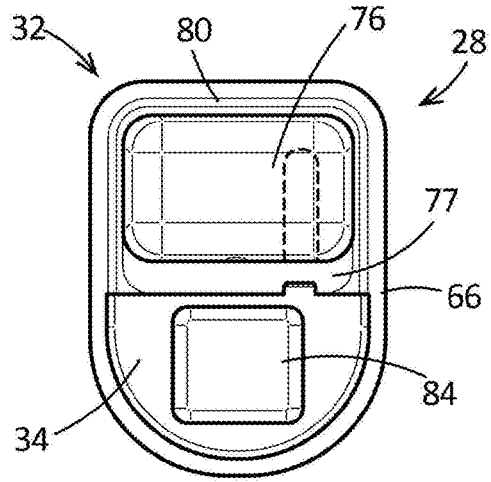
Figure 14J:
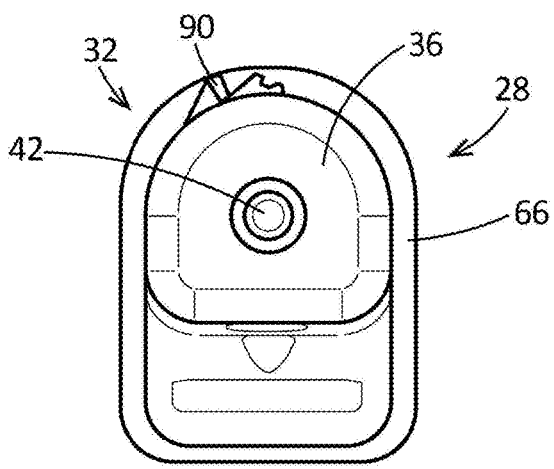

As shown in FIG. 13, the battery 54 of the electronic hearing device 28 may be accessed by pulling out a battery compartment drawer 90.

As shown in FIGS. 6 and 7, the profile of the side surface 38 of the housing 32 is configured to correspond to the inner profile 18 of the recessed cavity 16 of the custom earplug 12. The profile of the side surface 38 and the inner profile 18 are configured so that the electronic hearing device 28 is held securely within the custom earplug 12, but also to allow the electronic hearing device 28 to easily be removed and replaced by the user, such as when the charge on the battery 54 is depleted or when the device 28 needs to be cleaned or dried.

In a preferred embodiment, at least one annular retainer protrusion 66 extends outward from the cylindrical side surface 38 of the housing 32. The retainer protrusion 66 is received into a corresponding annular retainer channel 64 in the inner surface of the recessed cavity 16 of the custom earplug 12. This arrangement ensures that the electronic hearing device 28 is retained within the recessed cavity 16 until a user intentionally removes the device 28 from the cavity 16 by applying a sufficient pulling force. As one of ordinary skill in the art will appreciate, a sufficient pulling force would be enough force to disengage the retainer protrusion 66 of the housing 32 from the compliant material—such as silicone—of the retainer channel 64 in the custom earplug 12.

In the embodiment depicted in FIGS. 5C, 5D, 5J, 6 and 7, the sound opening 42 of the electronic hearing device 28 is centered in the housing 32, and the first opening 24 is centered in the cavity 16 of the custom earplug 12. This ensures that the sound opening 42 is always properly aligned with the first opening 24, no matter how the device 28 is rotated with respect to the cavity 16 of the custom earplug 12.

Third Embodiment

Figure 15:
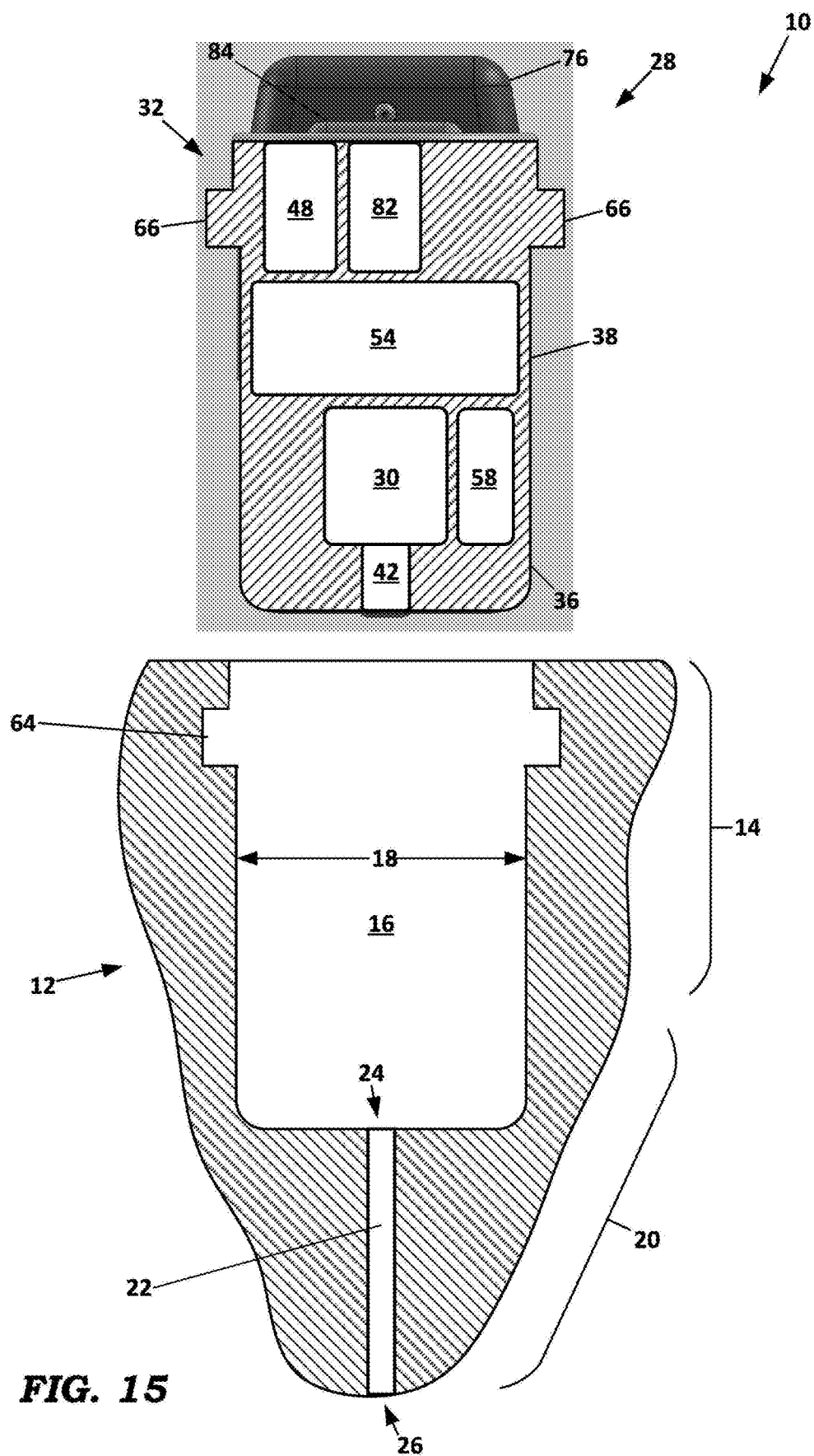
FIG. 15 depicts a cross-sectional side view of a hearing protection system in which the electronic hearing device is removed from the custom earplug according to the third embodiment.
Figure 16:
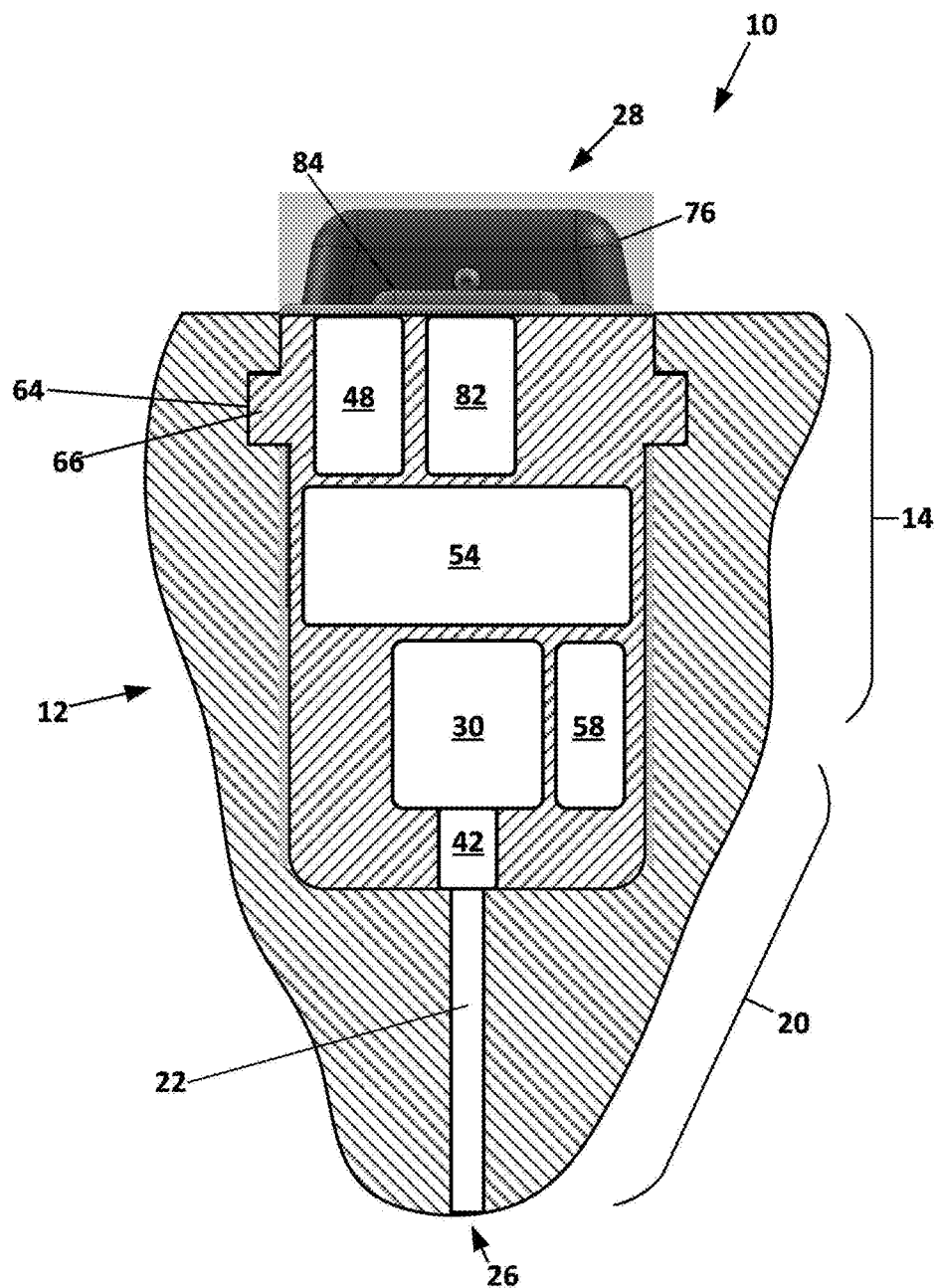
FIG. 16 depicts a cross-sectional side view of the hearing protection system in which the electronic hearing device is inserted into the custom earplug according to the third embodiment.
Figure 19A:
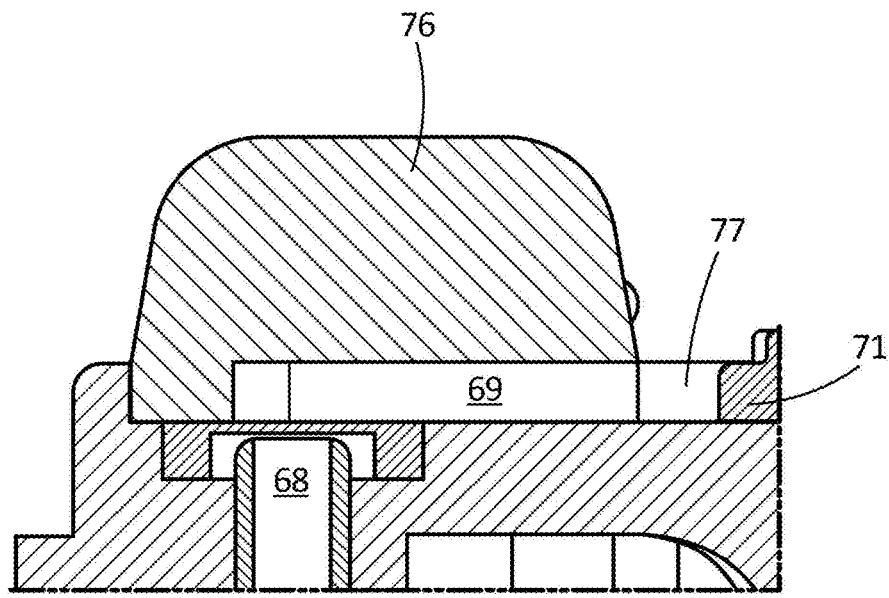
FIGS. 19A and 19B depict cross section views of a slider and microphone aperture according to the third embodiment.
Figure 19B:
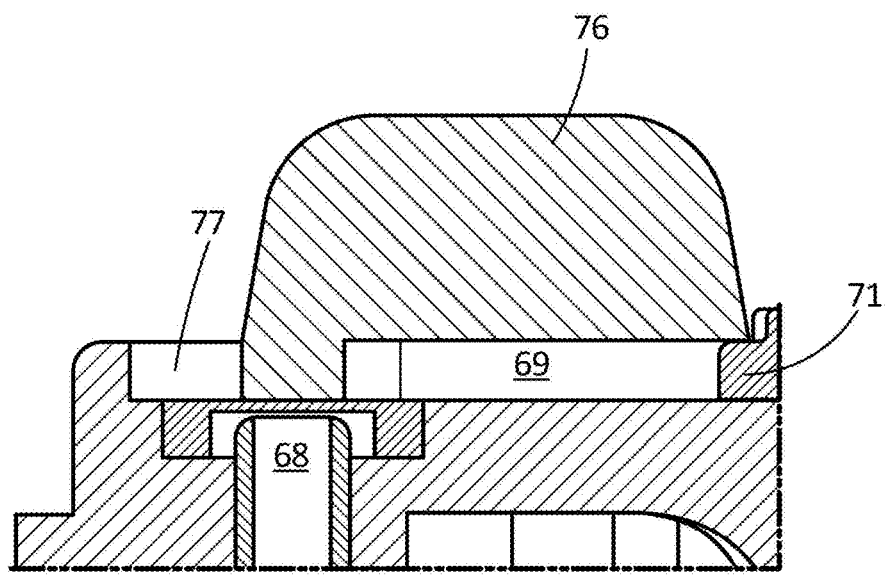

FIGS. 9, 10, 14A-14J, 15, 16, 17A-17B, 18A-18B, 19A-19B and 20A-20B depict a third embodiment of a custom electronic switchable hearing protection system 10. As shown in FIGS. 15 and 16, the hearing protection system 10 includes a custom earplug 12 having a first portion 14 and a second portion 20. The first portion 14, which is configured to fit in the user's outer ear, contains a recessed cavity 16 having an inner profile 18. The second portion 20 is configured to precisely fit into a user's ear canal. In a preferred embodiment, the custom earplug 12 is molded from a compliant material, such as silicone, soft vinyl or latex, using a mold having dimensions based on laser measurements, digital imaging, or digital modeling of the user's ear canal. Alternatively, an impression of the ear canal may be made by casting. In some alternative embodiments, the custom earplug 12 may be formed by 3D printing based on a digital model or digital image.

In a preferred embodiment, the custom earplug 12 includes a sound tube 22 extending through the first portion 14 and the second portion 20 of the custom earplug 12. The sound tube includes a first opening 24 disposed within the recessed cavity 16 of the first portion 14 and a second opening 26 disposed at a distal end of the second portion 20. In some configurations of the system 10, the sound tube 22 allows sound to travel through the first opening 24 to the second opening 26 and then into the user's ear canal.

In a preferred embodiment, the hearing protection system 10 includes an electronic hearing device 28 that is configured to be inserted into the recessed cavity 16 of the custom earplug 12. As shown in FIG. 9, the electronic hearing device 28 includes a microphone assembly 50 for receiving external sound, programmable electronics 58 for processing and amplifying the received sound according to the user's preferences, first and second switching devices 48 and 82, such as pushbutton, rocker, or toggle switches, for controlling the electronics 58, a battery 54 for powering the electronics 58, and a speaker assembly 30 (also referred to as a receiver) for generating the processed and amplified sound. The battery 54 may be replaceable or rechargeable.

The electronic hearing device 28 includes a housing 32 having a front surface 34 and an opposing rear surface 36. In the preferred embodiment, the housing 32 includes a side surface 38 disposed between the front and rear surfaces 34 and 36. A microphone aperture 68 is disposed in the upper surface 34 of the housing 32 through which sound travels to the microphone assembly 50. A sound opening 42 is disposed in the rear surface 36 of the housing through which the sound generated by the speaker assembly 30 is emitted. In the preferred embodiment, the housing 32 of the electronic hearing device 28 is molded from a sturdy plastic, such as Photoplastic, or formed from metal. In some embodiments, the housing 32 is an acrylic material in which the electronic components are encased (potted) for protection from moisture.

In some preferred embodiments, the electronics 58 incorporate programmable digital signal processing that provides for personalizing the electronic hearing device 28 to accommodate the hearing needs of the user based on a preloaded algorithm or a user-selected algorithm. Examples of hearing assistance devices that incorporate programmable digital signal processing are described in U.S. Pat. Nos. 7,974,716B2, 8,265,314B2, 8,284,968B2, 8,396,237B2, 8,077,890B2, 8,472,634B2, 8,811,642B2 and 9,031,272B2, the entire disclosures of which are incorporated herein by reference. In some embodiments, a single preset program is loaded on the device 28 that provides a normal level of amplification for a typical user who has no hearing loss, in which case no user selection of programs is needed. In some embodiments, the single preset program is optimized for the individual user's hearing profile.

In preferred embodiments, when a loud noise is detected by the microphone assembly 50, the programmable electronics 58 of the electronic hearing device 28 utilize a fast compression algorithm to quickly attenuate the corresponding sound provided to the speaker assembly 30 to prevent hearing damage. The fast compression algorithm preferably has a fast-acting attack time of between 0.5 msec and 20 msec to implement the attenuation. In a preferred embodiment, the programmable electronics 58 remove the attenuation when the excessively loud noise ceases, thereby returning to normal operation. The attack time is preferably a programmable preset value.

As shown in FIGS. 14A, 14B, 14E-14I, 15, 16, 17A-17B, 18A-18B and 19A-19B, the third embodiment of the electronic hearing device 28 incorporates a slider 76 that is operable to slide relative to the front surface 34 of the housing 32 of the electronic hearing device 28. The slider 76 includes an internal slider cavity 75 that receives the toggle lever 70 of the first switching device 48, and a sound channel 69 that is aligned with the microphone aperture 68. The slider 76 is preferably disposed within a slider recess 77 in the front surface 34 of the housing. Inner and outer edges of the slider recess 77 limit the movement of the slider 76 between first and second positions. As shown in the various figures, the slider 76 is large enough to substantially cover the toggle lever 70 throughout the range of movement of the slider 76, thereby preventing entry of particulate matter that could damage the first switching device 48.

According to the third embodiment, when the slider 76 is moved to the first position, the toggle lever 70 of the first switching device 48 is moved to a first switch position (shown in FIGS. 17B, 18B and 19B), and when the slider 76 is moved to the second position (shown in FIGS. 17A, 18A and 19A), the toggle lever 70 of the first switching device 48 is moved to a second switch position. When the first switching device 48 is in the first switch position, the electronics 58 are turned off or otherwise deactivated, such that sounds received by the microphone assembly 50 are not amplified and provided to the speaker assembly 30. When the first switching device 48 is in the second switch position, the electronics 58 are activated, such that sounds received by the microphone assembly 50 are amplified and provided to the speaker assembly 30.

Also, when the slider 76 is in the first position, the microphone aperture 68 is covered by the slider 76, and the open end of the sound channel 69 receives and is blocked by the protrusion 71 at the edge of the recess 77. This prevents dust and moisture from entering the aperture 68 when the microphone assembly 50 is not in use. When the slider 76 is in the second position, the microphone aperture 68 is in communication with the sound channel 69, thereby allowing sound to enter the microphone aperture 68 when the microphone assembly 50 is in use.

As shown in FIGS. 14A, 14B, 14E, 14G, 14H and 14I, the third embodiment of the electronic hearing device 28 includes a programming button 84 extending outward from the front surface 34 of the housing 32. The programming button 84 is operable to be pushed downward by a user to press the second switching device 82 disposed within the housing 32 of the electronic hearing device 28. Pressing the second switching device 82 allows the user to switch between and select different settings, including at least two different signal processing algorithms/programs stored in the electronics 58. The second switching device 82 may also be used to control the volume of the amplification provided by the electronics 58 and speaker assembly 30. In various embodiments, the programming button 84 may be operated by tapping, pressing, sliding, or using a magnet.

Figure 20A:
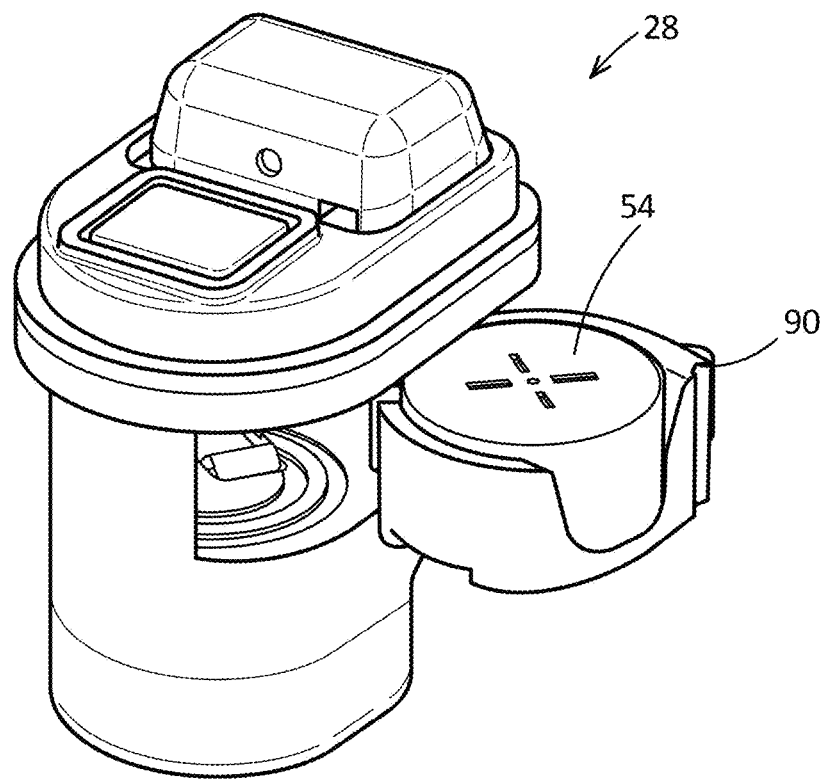
FIGS. 20A and 20B depict an open battery compartment with a battery according to the third embodiment.
Figure 20B:
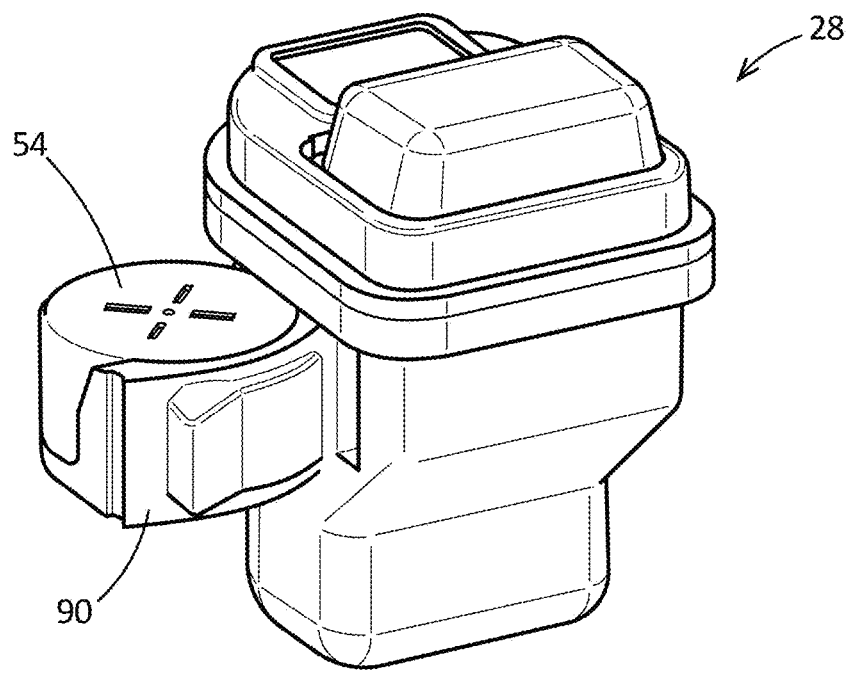

As shown in FIGS. 20A and 20B, the battery 54 of the electronic hearing device 28 may be accessed by swinging open a battery compartment 90 that is hinged to the housing 32. It will be appreciated that in some embodiments the battery compartment 90 may be hinged on the right side of the housing 32, while in other embodiments it may be hinged on the left side.

As shown in FIGS. 15 and 16, the profile of the side surface 38 of the housing 32 is configured to correspond to the inner profile 18 of the recessed cavity 16 of the custom earplug 12. The profile of the side surface 38 and the inner profile 18 are configured so that the electronic hearing device 28 is held securely within the custom earplug 12, but also to allow the electronic hearing device 28 to easily be removed and replaced by the user, such as when the charge on the battery 54 is depleted or when the device 28 needs to be cleaned or dried. In some embodiments, the device 28 includes a pull wire that the user may grasp and pull to remove the device 28 from the earplug 12.

In a preferred embodiment, at least one annular retainer protrusion 66 extends outward from the side surface 38 of the housing 32. The retainer protrusion 66 is received into a corresponding retainer channel 64 in the inner surface of the recessed cavity 16 of the custom earplug 12. This arrangement ensures that the electronic hearing device 28 is retained within the recessed cavity 16 until a user intentionally removes the device 28 from the cavity 16 by applying a sufficient pulling force. As one of ordinary skill in the art will appreciate, a sufficient pulling force would be enough force to disengage the retainer protrusion 66 of the housing 32 from the compliant material of the retainer channel 64 in the custom earplug 12.

Wireless Communication Embodiments

Some embodiments of the electronic hearing device 28 include a wireless communication interface which may be a Wi-Fi interface, Bluetooth interface, Bluetooth low energy interface, Auracast interface or other type of interface that is operable to receive wireless instructions for programming or controlling the electronics 58 using an external computing device. The wireless communication interface may also be used to provide voice communications to the user from a command center.

Figure 21:
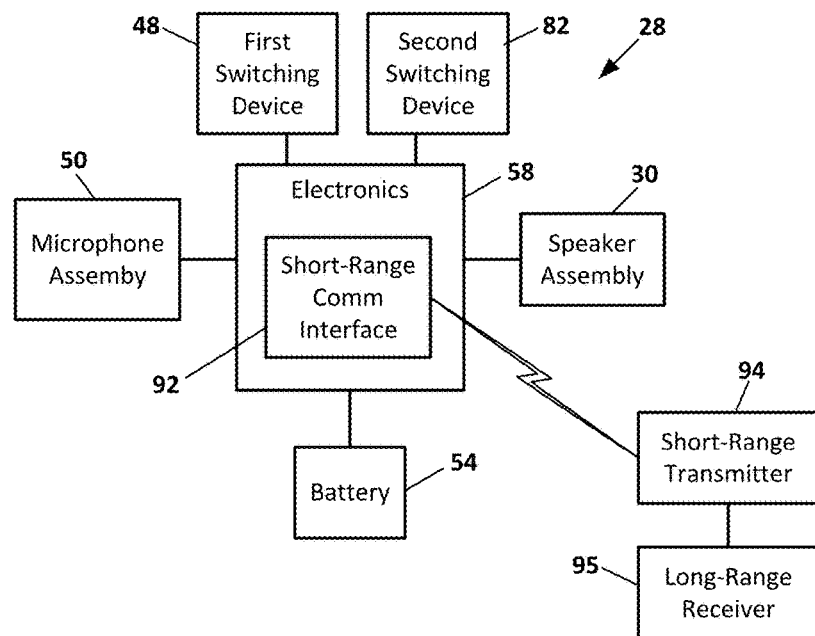
FIG. 21 depicts a functional block diagram of embodiments of the system.

FIG. 21 depicts an embodiment of the electronic hearing device 28 that may be used by the military. This embodiment includes a short-range wireless communication interface 92, such as a nearfield communication (NFC) interface or an induction coil interface, that is operable to receive communications from an external short-range wireless transmitter 94. In a preferred embodiment, the short-range wireless transmitter 94 uses an NFC peer-to-peer (P2P) communication protocol. The NFC P2P protocol provides for transferring information, such as audio data, between two devices over very short distances, such as less than six inches. In the embodiment of FIG. 21, the short-range transmitter 94 is interfaced with a long-range wireless receiver 95 that receives encrypted wireless communications from a command center. In one preferred embodiment, the short-range transmitter 94 and the long-range receiver 95 are built into or attached to a helmet or other headgear worn by military personnel. The receiver 95 decrypts the command communications and converts them into audio files that are compatible with the NFC P2P protocol so that the short-range transmitter 94 can communicate them to the interface 92. The electronics 58 of the electronic hearing device 28 generates signals based on the audio data from the interface 92 and provide the signals to the speaker assembly 30 for generation of corresponding sound information for the user. It will be appreciated that the embodiment of FIG. 21 is not limited to the use of the NFC P2P protocol for short-range communications, as other protocols could be implemented.

Noise Dosimeter Embodiments

Figure 22:
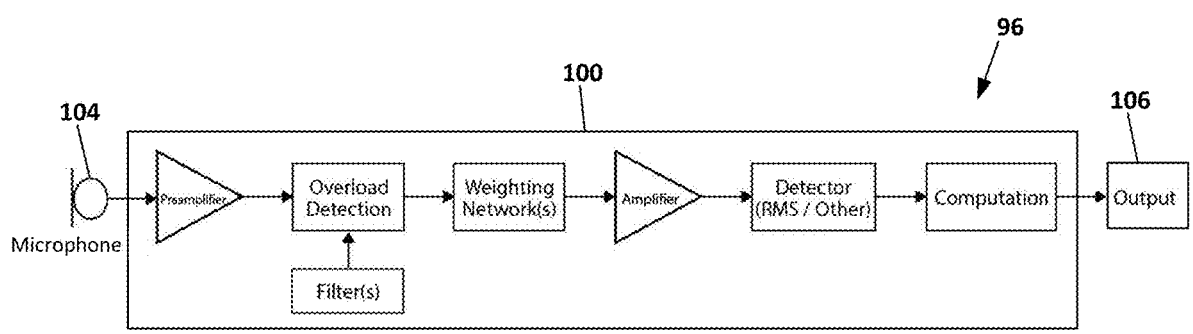
FIG. 22 depicts a functional block diagram of a noise dosimeter according to an embodiment of the system.

Some embodiments of the hearing protection system 10 include a noise dosimeter for measuring noise levels in the environment of the user of the hearing protection system 10. As will be appreciated by one of ordinary skill in the art, a noise dosimeter is a type of sound level meter that provides an integrated measurement of the amount of noise to which a person is exposed over a period of time. A functional block diagram of an exemplary noise dosimeter 96 is depicted in FIG. 22. Other examples of noise dosimeter circuits may be found in U.S. Pat. Nos. 3,977,257 and 6,826,515, the entire contents of which are incorporated herein by reference.

The noise dosimeter 96 includes a microphone 104 for receiving sound in the vicinity of the user of the hearing protection system 10, and electronics 100 for conditioning and processing audio signals from the microphone 104. The electronics 100 generate noise exposure measurement data in the form of a numerical value or other type of output or signal that represents the level of noise exposure integrated over a period of time. The noise exposure measurement data may be stored in memory within the electronics 100 and accessed via an output interface 106, such as a USB connector or other type of data interface connector. In some embodiments, the output interface 106 comprises a wireless data interface for wirelessly communicating the noise exposure measurement data to an external device.

Figure 23:
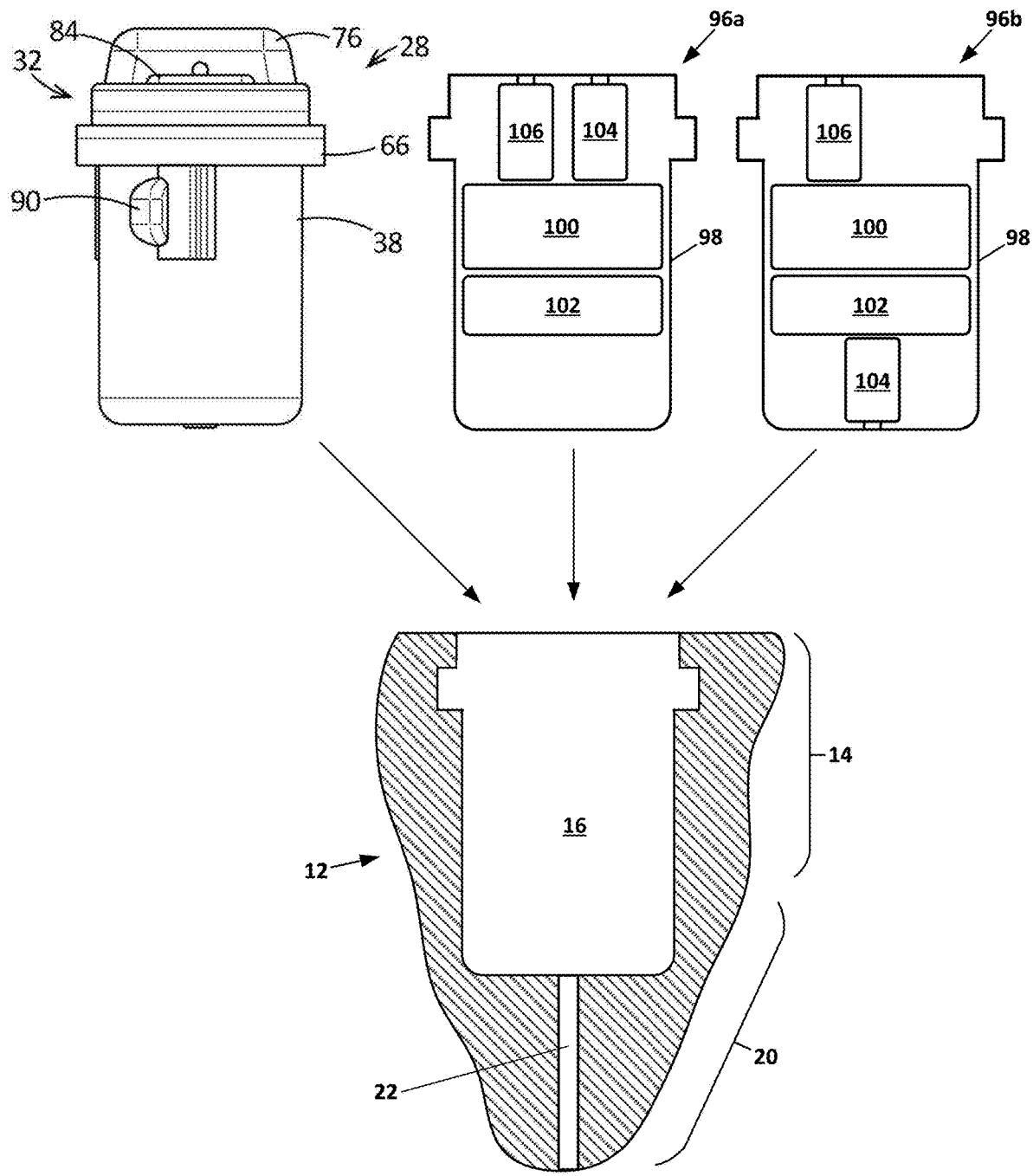
FIG. 23 depicts a hearing protection kit in which the electronic hearing device and noise dosimeters are removed from the earplug according to an embodiment.

As depicted in FIG. 23, at least two different dosimeter embodiments 96a and 96b may be used in conjunction with the earplug 12 of the hearing protection system 10. In both embodiments, the microphone 104, electronics 100, a battery 102 for powering the electronics, and the output port 106 are disposed in a housing 98. It will be appreciated that in both embodiments, the microphone 104 is disposed in or near a sound entry aperture in the housing 98. In preferred embodiments, the housing 98 has the same outer profile as the housing 32 of the electronic hearing device 28, and it is inserted into and held within the cavity 16 of the earplug 12 in the same manner as the housing 32, as described herein.

As shown in FIG. 23, the microphone 104 of the dosimeter 96a is positioned in or adjacent a sound entry aperture in the outer surface of the housing 98, which is the surface that is exposed to the environment when the dosimeter 96a is disposed within the cavity 16 of the earplug 12. In this position, the microphone 104 receives external sound from the environment near the user when the earplug 12 is inserted in the user's ear canal and concha. Thus, the dosimeter 96a is configured to measure external environmental noise to which the user would be exposed over time if the user is not wearing any hearing protection.

With continued reference to FIG. 23, the microphone 104 of the dosimeter 96b is positioned in or adjacent an aperture in the housing 98 that is adjacent the opening 24 of the sound tube 22. Because the sound tube 22 is open to user's ear canal when the earplug 12 is inserted therein, the microphone 104 receives sound from within the user's ear canal. Thus, the dosimeter 96b is configured to measure noise to which the user is exposed over time while the user is wearing the hearing protection system 10.

When used together as a dosimeter measurement system, a comparison of the noise measurements made using the two dosimeters 96a and 96b can indicate how effective the hearing protection system 10 is in reducing noise to which the user's inner ear is exposed. This assumes that the external noise present in the time period during which dosimeter 96a makes its measurement is substantially the same as the external noise present in the time period during which dosimeter 96b makes its measurement.

In some embodiments, the dosimeter 96 includes two microphones 104, with one disposed for measuring external environmental noise, as in embodiment 96a, and one disposed for measuring noise within the user's ear canal, as in embodiment 96b. It will be appreciated that the electronics 100 of this embodiment preferably incorporate two parallel measurement channels for processing the audio information from the two microphones 104 simultaneously. With this arrangement, the two measurements are made during exactly the same time period, which eliminate the measurement uncertainty introduced by making measurements during different time periods.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A hearing protection system comprising:
   an earplug formed from a compliant material and comprising:
      a first portion configured to be disposed in a user's outer ear, the first portion including a recessed cavity having an inner profile;
      a second portion having a distal end configured for insertion into the user's ear canal, the second portion including a sound tube having:
         a first opening disposed within the recessed cavity of the first portion; and
         a second opening disposed at the distal end of the second portion; and
   an electronic hearing device configured to be removably inserted into the recessed cavity of the earplug, the electronic hearing device comprising:
      a microphone for receiving external sound and generating an electrical sound signal based thereon;
      electronics that amplify the electrical sound signal, shut off sound amplification to protect the user when a loud noise is detected, and resume sound amplification after the loud noise ends;
      a short-range communication interface for receiving a short-range communication signal that carries information;
      a speaker assembly for generating sound based on one or both of the electrical sound signal and the information from the short-range communication signal; and
      a housing in which the microphone, speaker assembly, electronics and short-range communication interface are disposed, the housing having:
         a front surface, a rear surface opposite the front surface, and a side surface disposed between the front and rear surfaces; and
         a sound aperture disposed in one of the surfaces of the housing for emitting the sound from the speaker assembly, the sound aperture aligned with the first opening of the sound tube, thereby permitting the sound generated by the speaker assembly to propagate through the sound tube to the second opening.

2. The hearing protection system according to claim 1 wherein the electronics include fast compression programming that shuts off sound amplification when a loud noise is detected, and resumes amplification after the loud noise ends.

3. The hearing protection system according to claim 1 wherein the short-range communication interface comprises a nearfield communication (NFC) interface.

4. The hearing protection system according to claim 1 wherein the short-range communication interface is configured to receive the short-range communication signal carrying audio information.

5. The hearing protection system according to claim 1 further comprising a short-range transmitter disposed externally to the earplug and the housing of the electronic hearing device, the short-range transmitter for transmitting the short-range communication signal to the short-range communication interface.

6. The hearing protection system according to claim 1 further comprising a long-range receiver disposed externally to the earplug and the housing of the electronic hearing device, the long-range receiver in electrical communication with the short-range transmitter, the long-range receiver configured to receive wireless communications transmitted from a command center.

7. The hearing protection system according to claim 6 further comprising headgear configured to be worn by the user, wherein the short-range transmitter and the long-range receiver are attached to or disposed within the headgear.

8. The hearing protection system according to claim 1, wherein at least a portion of the side surface of the housing extends outward from the recessed cavity in the first portion of the earplug, so that the side surface can be gripped by the user for pulling the housing out of the recessed cavity.

9. The hearing protection system according to claim 1, wherein the electronic hearing device further comprises a switching device configured to be operated by the user to activate or deactivate the electronics.

10. The hearing protection system according to claim 1 wherein the electronic hearing device further comprises:
 a switching device disposed within the housing; and
 a programming button disposed adjacent the front surface of the housing, the programming button operable to be pushed downward by the user to engage the switching device which causes the electronics to switch between multiple signal processing algorithms.

11. The hearing protection system according to claim 1, wherein the inner profile of the recessed cavity substantially matches the side and rear surfaces of the housing of the electronic hearing device.

12. The hearing protection system according to claim 1, wherein the electronic hearing device includes a protrusion extending outward from the side surface of the housing, and wherein the inner profile of the recessed cavity includes a channel configured to receive the protrusion on the housing so as to secure the housing within the recessed cavity while allowing the housing to be removed from the recessed cavity as a sufficient pulling force is applied to the housing.

13. The hearing protection system according to claim 1, wherein the electronics include digital signal processing that is programmable to provide customized sound amplification according to a hearing profile of the user.

* * * * *